US010045529B2

(12) United States Patent
Griese et al.

(10) Patent No.: US 10,045,529 B2
(45) Date of Patent: *Aug. 14, 2018

(54) QUAT CLEANER WITH GLYCERIN ETHER ETHOXYLATES

(71) Applicant: Ecolab USA Inc., St. Paul, MN (US)

(72) Inventors: Gregory G. Griese, Hudson, WI (US); Carter M. Silvernail, Burnsville, MN (US); David D. McSherry, St. Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/446,491

(22) Filed: Jul. 30, 2014

(65) Prior Publication Data

US 2014/0343157 A1    Nov. 20, 2014

Related U.S. Application Data

(63) Continuation-in-part of application No. 13/794,871, filed on Mar. 12, 2013, now abandoned.

(60) Provisional application No. 61/666,374, filed on Jun. 29, 2012.

(51) Int. Cl.
| | | |
|---|---|---|
| *A01N 33/12* | (2006.01) | |
| *A01N 25/30* | (2006.01) | |
| *A01N 31/02* | (2006.01) | |
| *C11D 1/835* | (2006.01) | |
| *C11D 3/48* | (2006.01) | |
| *C11D 3/20* | (2006.01) | |
| *C08G 65/26* | (2006.01) | |
| *C11D 1/722* | (2006.01) | |
| *C11D 1/62* | (2006.01) | |

(52) U.S. Cl.
CPC ............ *A01N 33/12* (2013.01); *A01N 25/30* (2013.01); *A01N 31/02* (2013.01); *C08G 65/2609* (2013.01); *C11D 1/835* (2013.01); *C11D 3/2068* (2013.01); *C11D 3/48* (2013.01); *C11D 1/62* (2013.01); *C11D 1/722* (2013.01)

(58) Field of Classification Search
CPC ................................ A01N 33/12; A01N 25/30
See application file for complete search history.

(56) References Cited

U.S. PATENT DOCUMENTS

| | | | |
|---|---|---|---|
| 4,174,304 A * | 11/1979 | Flanagan ................. | C11D 1/62 134/38 |
| 4,298,764 A | 11/1981 | Berkowitz | |
| 5,176,850 A | 1/1993 | O'Neil | |
| 5,403,509 A | 4/1995 | Pujol et al. | |
| 5,420,312 A | 5/1995 | Andrews et al. | |
| 5,549,840 A | 8/1996 | Mondin et al. | |
| 5,593,958 A | 1/1997 | Mondin et al. | |
| 5,716,925 A | 2/1998 | Mondin et al. | |
| 5,776,880 A | 7/1998 | Mondin et al. | |
| 5,942,482 A | 8/1999 | Zocchi et al. | |
| 6,337,352 B1 | 1/2002 | Millium | |
| 6,423,678 B1 | 7/2002 | Brumbaugh et al. | |
| 6,717,019 B2 | 4/2004 | Lassila | |
| 8,221,733 B2 | 7/2012 | Lichtenberg et al. | |
| 2002/0151455 A1* | 10/2002 | Sano ....................... | C11D 1/62 510/504 |
| 2004/0214740 A1 | 10/2004 | Barberan et al. | |
| 2010/0197559 A1 | 8/2010 | Kotera et al. | |
| 2011/0009676 A1 | 1/2011 | Beilfuss et al. | |

FOREIGN PATENT DOCUMENTS

| | | |
|---|---|---|
| EP | 0275710 A1 | 7/1988 |
| EP | 0586323 B2 | 11/2005 |
| EP | 1672054 A1 | 6/2006 |
| JP | 1979044039 A | 4/1979 |
| JP | 6-240480 A | 8/1994 |
| JP | 6-346259 A | 12/1994 |
| JP | 11-503784 A | 3/1999 |
| JP | 2008037763 A | 2/2008 |
| JP | 2008-239942 A | 10/2008 |
| JP | 2008-297332 A | 12/2008 |
| JP | 2012-82357 A | 4/2012 |
| WO | 2012026710 A2 | 3/2012 |

OTHER PUBLICATIONS

JP 6-240480, Niihon Parkerizing—English Machine Translation, Aug. 30, 1994.
JP 6-346259, Kao—English Machine Translation, Dec. 20, 1994.
JP 11-503784, Alain Milium—English Machine Translation, Mar. 30, 1999.
JP 2008-239942, Sanyo Chemical Industries—English Machine Translation, Oct. 9, 2008.
JP 2008-297332, Sanyo Chemical Industries—English Machine Translation, Dec. 11, 2008.
JP 2012-82357, Sanyo Chemical Industries—English Translation, Apr. 26, 2012.
Marinova, K.G., et al., "Impact of the Surfactant Structure on the Foaming/Defoaming Performance of Nonionic Block Copolymers in Na Caseinate Solutions", Bulg. J. Phys. 39, pp. 53-64, Dec. 31, 2012.

(Continued)

*Primary Examiner* — David J Blanchard
*Assistant Examiner* — Nicole P Babson
(74) *Attorney, Agent, or Firm* — McKee, Voorhees & Sease, PLC

(57) ABSTRACT

The present invention relates to sanitizing compositions containing glycerin ether ethoxylate solfactant compounds and cationic active antimicrobial agents containing quaternary ammonium groups. Beneficially the compositions provide sanitizing efficacy without diminished performance requiring either increased concentrations of sanitizing agent and/or increased contact time for surfaces treated with the compositions. The compositions are suitable for use as antimicrobials and/or sanitizing agents in various formulations and methods of employing the same.

16 Claims, 10 Drawing Sheets

(56) References Cited

OTHER PUBLICATIONS

Evonik Industries, Sipernat and Aerosil for defoamer, Technical Information 1313=accessed from http://www.sipemat.com/sites/dc/Downloadcenter/Evonik/Products/SIPERNAT/ti1313_us_28s_wz_2011_11_einzelseiten.pdf.pdf, 28 pages, Mar. 28, 2014.

Von Phul, Stephen A., et al., "Antifoam: What Is It? How Does It Work? Why Do They Say to Limit Its Use?"=accessed from http://www.d-foam.com/files/Antifoam_What_Is_It.pdg, 10 pages, Mar. 28, 2014.

Air Products, "Tomadol Ethoxylated Alcohols Product Guide", Publication No. 1110-10-002-US, pp. 1-36, Jul. 17, 2014.

Baumann, Wolfgang J. et al., "Reactions of Aliphatic Methanesulfonates. I. Syntheses of Long-Chain Glyceryl-(1) Ethers", Long-Chain Glyceryl-(1) Ethers, Oct. 1964, pp. 3055-3057, Oct. 1964.

Eastman Chemical Company, "Safety Data Sheet" SDSUS/EN/08, Version: 2.4, 12 pages, Oct. 3, 2011.

Gu, Yanlong et al., "Heterogeneously catalyzed etherification of glycerol: new pathways for transformation of glycerol to more valuable chemicals", Ccommunication, Green Company, 10, pp. 164-167, 2008.

Queste, Sebastien et al., "Short chain glycerol 1-monoethers—a new class of green solvo-surfactants" Green Chemicstry, 8, pp. 822-830, 2006.

Ecolab USA Inc., PCT/US2013/030518, filing date Mar. 12, 2013, "The International Search Report and The Written Opinion of The International Searching Authority, or the Declaration", dated Jun. 17, 2013.

European Patent Office, "Extended European Search Report", issued in connection to European Application No. 13808992.5, dated Mar. 4, 2016, 9 pgs.

Kato, Yasuharu, et al., "Textile assistant for processing fiber and textile goods", STN Database Accession No. 80:122333, XP-002753391, 1 pg., Jan. 25, 2016.

Ogiwara, Michihiro, et al., "Cosmetics", STN Database Accession No. 91:96519, XP-002753392, 4 pgs. Jan. 25, 2016.

Naniwa, Kimiyoshi, et al., "Antiseptic agents containing alkyl glyceryl ether (poly)alkylene glycol derivatives, and cosmetics and detergents containing the same", STN Database Accession No. 148:245989, XP-002753393, 2 pgs. Jan. 25, 2016.

\* cited by examiner

QUAT CLEANER WITH GLYCERIN ETHER ETHOXYLATES

CROSS-REFERENCE TO RELATED APPLICATIONS

This application is a continuation-in-part of U.S. Ser. No. 13/794,871, filed Mar. 12, 2013, titled Glycerin Ether Ethoxylate Solfactants, which claims priority under 35 U.S.C. § 119 to provisional application U.S. Ser. No. 61/666,374, filed Jun. 29, 2012, titled Glycerin Ether Ethoxylate Surfactants, which are each herein incorporated by reference in their entirety.

FIELD OF THE INVENTION

The present invention relates to sanitizing compositions containing solfactant compounds having efficacy as both solvents and surfactants and sanitizing quaternary ammonium compounds. In particular, the present invention relates to compositions comprising glycerin ether ethoxylate compounds in combination with cationic active antimicrobial agents containing quaternary ammonium groups, and methods of using the compounds for cleaning and sanitation. The compositions of the present invention can be used as antimicrobials and/or sanitizing agents in various formulations to provide efficacy at minimized concentrations and time of exposure.

BACKGROUND OF THE INVENTION

There are continued needs for novel surfactants having improved surfactant characteristics. Desirable improvements to surfactants include characteristics affecting solubilization, gel formation, foam production and/or cloud points. In particular, the ability to employ surfactants having low surface tensions at low use levels and/or the ability to control foam characteristics of a surfactant have significant industrial importance. Extensive discussions of the fundamental properties and practical application of surfactants can be found in Kirk Othmer Encyclopedia of Chemical Technology, Fourth Edition, Volume 23, pp. 477-541, which is herein incorporated by reference in its entirety. Glycerin ethers represent a new class of emerging solvents, including glycerin-derived short-chain aliphatic ether or salts thereof. Various such solvents are disclosed for example in U.S. Patent Publication No. 2012/0309849, which is herein incorporated by reference in its entirety. These solvents can be used according to the invention to arrive at the novel solfactant class described herein. In particular, the glycerin ethers are particularly well suited for ethoxylation to arrive at the novel solfactants of the present invention.

Antimicrobial sanitizing compositions are known in the art for cleaning and sanitizing a variety of surfaces, including hard surfaces. Antimicrobial sanitizing compositions are used, for example, in the health care industry, hospitality industry, food service industry, food and beverage processing industry, and other commercial and/or institutional applications, along with those of individual consumers. The widespread use of antimicrobial sanitizing compositions indicates the importance consumers place on controlling bacteria and other microorganism populations.

Several different classes of antimicrobial sanitizing agents are used in commercially-available compositions. These include active ingredients selected from the following classes: phenolic compounds, carbanalide compounds, lower alcohols, surface active agents halogens, and carboxylic acids. Examples of specific antimicrobial agents include PCMX (para-chlorometa xylenol), Triclosan, Triclocarban, benzyl alcohol, quaternary ammonium compounds, iodine and iodine complexes and biguanides (e.g., chlorhexidine digluconate). Each of these classes has their own unique advantages and challenges.

Although there are myriad of sanitizing compositions available, there remains a need for improved cleaning performance of sanitizing formulations, such as the ability to employed reduced concentrations of sanitizing agents and/or reduced exposure time required for product performance (e.g. time a user is required to wait before cleaning a surface being contacted with the sanitizing composition). Many conventional sanitizing formulations employing quaternary ammonium compounds do not include certain classes of surfactants, such as alcohol ethoxylates, in the formulations due to diminished performance observed, requiring increased sanitizing concentrations of the quaternary ammonium compound and/or increased exposure time for efficacy. Thus, a need exists for additional efficacious antimicrobial sanitizing formulations containing quaternary ammonium compounds. The present invention is directed to such sanitizing compositions.

Accordingly, it is an objective of the claimed invention to develop sanitizing compositions comprising quaternary ammonium compounds in combination with a novel class of compounds referred to as "solfactants" having improved surfactant and solvent characteristics to either replace or use in combination with alcohol ethoxylates, alkoxylates, and/or propoxylates in various formulations.

A further object of the invention is to provide methods of cleaning and sanitizing employing compositions comprising the glycerin ether ethoxylate solfactants and sanitizing quaternary ammonium compounds.

The above-mentioned disadvantages of current antimicrobial sanitizing compositions are addressed by embodiments of the present invention and will be understood by reading and studying the following specification. The following summary is made by way of example and not by way of limitation. It is merely provided to aid the reader in understanding some of the aspects of the invention. Other objects, advantages and features of the present invention will become apparent from the following specification taken in conjunction with the accompanying drawings.

BRIEF SUMMARY OF THE INVENTION

An advantage of the invention is a sanitizing composition employing the novel solfactant systems in combination with sanitizing quaternary ammonium compounds. In some aspects, the solfactants are suitable for replacing alcohol ethoxylates, alkoxylates, and/or propoxylates. In an embodiment, the present invention is directed to a sanitizing composition comprising: a quaternary ammonium containing compound or a salt thereof; and a solfactant compound according to at least one of the following formulas:

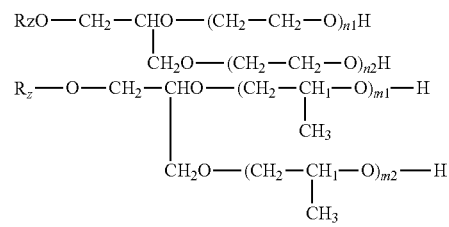

-continued

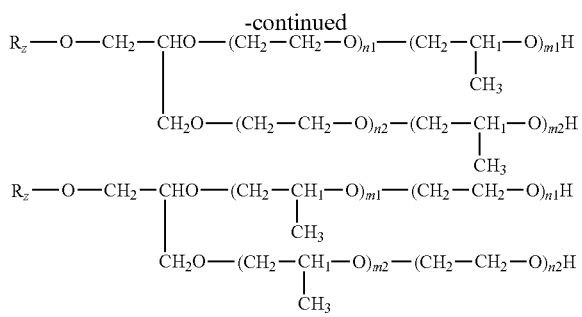

In another embodiment, the present invention is directed to a method of employing the sanitizing compositions comprising: contacting a surface, article and/or substrate in need of sanitizing with the solfactant and a sanitizing quaternary ammonium compound or salt thereof.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
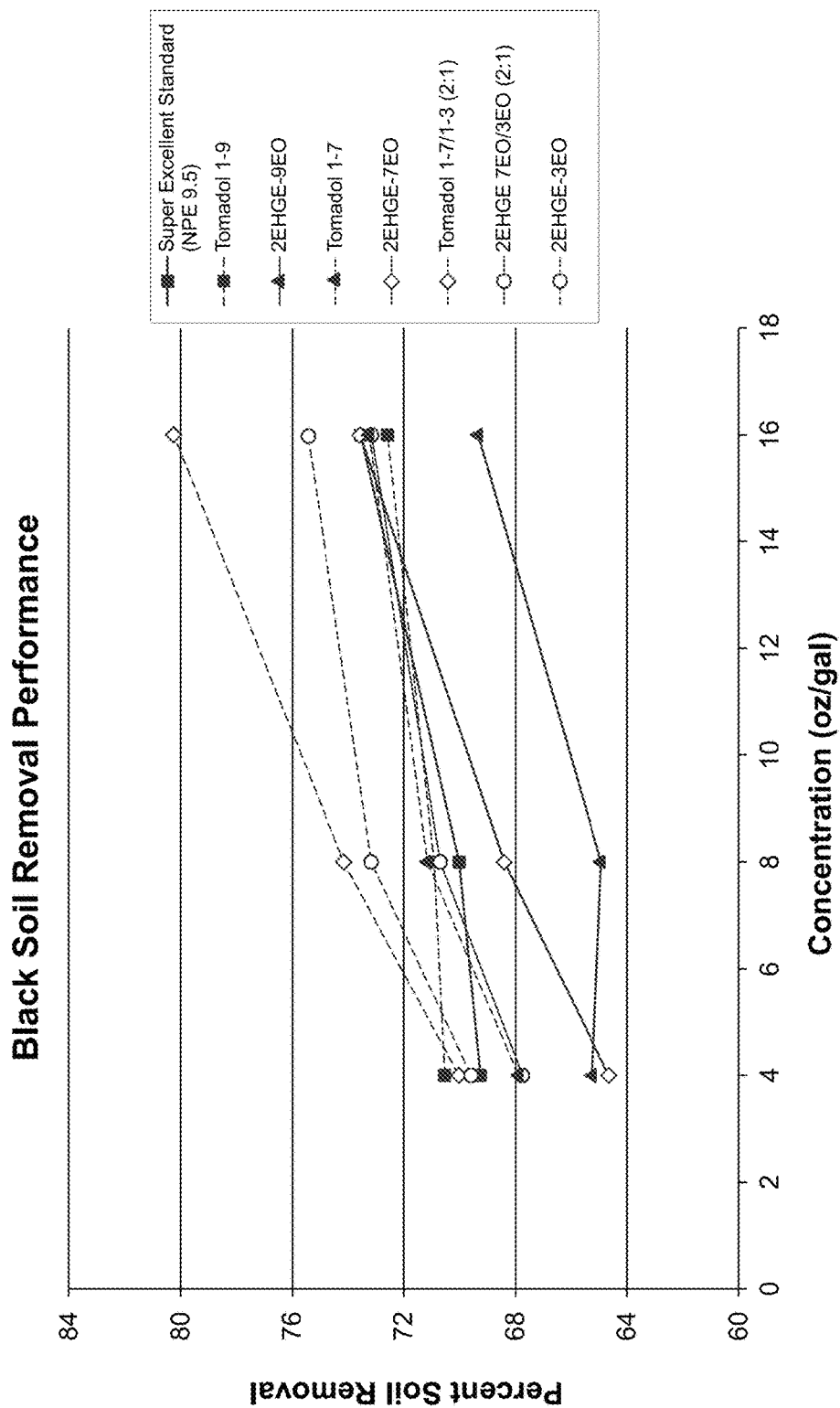
FIG. 1 shows a graph of various cleaning compositions containing the glycerin ether ethoxylate solfactants according to the invention, in comparison to a control composition (Super Excellent (with NPE 9.5)) and various equivalent ethoxylated alcohol based compositions on cleaning of black soils.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to sanitizing compositions containing glycerin ether ethoxylate solfactants and quaternary ammonium compounds. The compositions have a variety of advantages over conventional sanitizing compositions which are not customarily formulated with certain surfactants due to decreased sanitizing performance. In an aspect, skilled artisans in need of efficient sanitizing efficacy do not customarily combine alcohol ethoxylate surfactants with quaternary ammonium compounds, as diminished performance is observed requiring increased exposure time and/or concentrations to provide desirable sanitizing efficacy. Beneficially, the compositions of the present invention provide an efficacious combination of sanitizing quaternary ammonium compositions and solfactants which outperform the combination of the sanitizing compositions containing alcohol ethoxylates. As a further benefit to certain formulations, the glycerin ether ethoxylates have a low viscosity and formulation capabilities as both surfactants and solvents. The compositions according to the invention provide simultaneous cleaning and sanitizing efficacy.

It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range. So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including hetero aromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

An "antiredeposition agent" refers to a compound that helps keep suspended in water instead of redepositing onto the object being cleaned. Antiredeposition agents are useful in the present invention to assist in reducing redepositing of the removed soil onto the surface being cleaned.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, auto dish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the term "hard surface" includes showers, sinks, toilets, bathtubs, countertops, windows, mirrors, transportation vehicles, floors, and the like. These surfaces can be those typified as "hard surfaces" (such as walls, floors, bed-pans, etc.) or fabric surfaces, e.g., knit, woven, and non-woven surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with a composition according to the present invention. As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

The term "microemulsion" as used herein, refers to a thermodynamically stable liquid dispersion of one liquid phase into another that is stabilized by an interfacial film of surfactant. According to the invention, the microemulsion forms an interface with the surfactant between the two immiscible phases of oil and water.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the phrase "plant" or "plant product" includes any plant substance or plant-derived substance. Plant products include, but are not limited to, seeds, nuts, nut meats, cut flowers, plants or crops grown or stored in a greenhouse, house plants, and the like. Plant products include many animal feeds.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.9% reduction (3-log order reduction). In an aspect, sanitizers according to the invention provide at least a 99.9% reduction (3-log order reduction) within 30 seconds at room temperature. These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). The term "solvent" refers to an organic material or mixture of such materials suitable for cleaning, degreasing or stripping the desired surface, coupling, coalescing or adjusting viscosity.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both, when using the substitute solfactant(s) according to the invention. This degree of cleanliness may, depending on the particular cleaning product and particular substrate, correspond to a general absence of visible soils, or to some lesser degree of cleanliness.

The term "surfactant" or "surface active agent" refers to an organic chemical that when added to a liquid changes the properties of that liquid at a surface. In comparison, as used herein, the term "solfactant" refers to an organic chemical that when added to a liquid changes the properties of that liquid at a surface, specifically including the adjustment of the viscosity of a composition (e.g. handle ability or ease of use of the compositions). In particular, solfactant refers to a compound having the beneficial properties of both a surfactant and a solvent.

The terms "vehicle" or "car" as used herein, refer to any transportation conveyance including without limitation, automobiles, trucks, sport utility vehicles, buses, trucks, motorcycles, monorails, diesel locomotives, passenger coaches, small single engine private airplanes, corporate jet aircraft, commercial airline equipment, etc.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components/ingredients and steps set forth for the present invention as well as other ingredients and/or production steps described herein. As used herein, "consisting essentially of" means that the methods and compositions may include additional steps, components or ingredients, but only if the additional steps, components or ingredients do not materially alter the basic and novel characteristics of the claimed methods and compositions.

While an understanding of the mechanism is not necessary to practice the present invention and while the present invention is not limited to any particular mechanism of action, it is contemplated that, in some embodiments, the novel glycerin ether ethoxylate solfactants are produced according to the disclosed methods for ethoxylation of glycerin ethers, such as using ethylene oxide for the ethoxylation methods. These and other methods are set forth in further detail according to the invention and are not intended to limit the scope of the invention set forth herein.

Sanitizing Compositions

Exemplary ranges of the sanitizing compositions according to the invention are shown in weight percentage of the liquid compositions. In some aspects the glycerin ether ethoxylates are suitable for a 1:1 replacement for alcohol ethoxylates, alkoxylates, and/or propoxylates.

| Material | First Exemplary Range wt-% | Second Exemplary Range wt-% | Third Exemplary Range wt-% | Fourth Exemplary Range wt-% |
|---|---|---|---|---|
| Water | 50-99.9 | 60-99.9 | 70-99.5 | 75-99.5 |
| Quaternary Ammonium Compounds | 0.001-60 | 0.01-50 | 0.05-40 | 0.1-30 |
| Glycerin Ether Ethoxylate | 0.01-50 | 0.01-30 | 0.1-25 | 0.5-20 |
| Additional Functional Ingredients | 0-40 | 0-25 | 0-20 | 0-15 |

The detergent compositions may include concentrate compositions or may be diluted to form use compositions. In general, a concentrate refers to a composition that is intended to be diluted with water to provide a use solution that contacts an object to provide the desired cleaning, sanitizing, or the like. The sanitizing composition contacting articles to be cleaned can be referred to as a concentrate or a use composition (or use solution) dependent upon the formulation employed in methods according to the invention. It should be understood that the concentration of the quaternary ammonium compound, glycerin ether ethoxylate, and other optional functional ingredients in the composition will vary depending on whether the detergent composition is provided as a concentrate or as a use solution.

A use solution may be prepared from the concentrate by diluting the concentrate with water at a dilution ratio that provides a use solution having desired sanitizing properties. The water that is used to dilute the concentrate to form the use composition can be referred to as water of dilution or a diluent, and can vary from one location to another. The typical dilution factor is between approximately 1 and approximately 10,000 but will depend on factors including amount of soils and/or microorganisms to be removed and the like. In an embodiment, the concentrate is diluted at a ratio of between about 1:64 and about 1:256 concentrate to water. In some embodiments, preferred dilution ratios include about 1:64, about 1:128 or about 1:256, which may also be directed for dilution of from ½ ounce per gallon of water, 1 ounce per gallon of water, or 2 ounce per gallon of water, respectively.

In an aspect of the invention, a use solution of the sanitizing composition provides at least about 50 ppm quaternary ammonium compound, at least about 100 ppm quaternary ammonium compound, at least about 200 ppm quaternary ammonium compound, up to about 5,000 ppm quaternary ammonium compound in a use solution, or up to about 20,000 ppm (2%) in a concentration solution, or preferably between about 200 ppm to about 800 ppm quaternary ammonium compound in a use solution. As one skilled in the art will ascertain, the concentration of quaternary ammonium compound can be decreased while maintaining sanitizing efficacy through the formulation of additional solvents, builders and/or surfactants. Beneficially, according to the invention, a use solution of the sanitizing composition may employ less than about 800 ppm, preferably less than about 500 ppm, more preferably less than about 200 ppm quaternary ammonium compound in combination with the solfactants described herein to provide sanitizing efficacy. In addition, without being limited according to the invention, all ranges recited are inclusive of the numbers defining the range and include each integer within the defined range.

Glycerin Ether Ethoxylate Solfactants

In an aspect, the compositions include from about 0.01 wt-%-50 wt-% glycerin ether ethoxylates, from about 0.01 wt-%-30 wt-% glycerin ether ethoxylates, from about 0.1 wt-%-25 wt-% glycerin ether ethoxylates, or more preferably from about 0.5 wt-%-20 wt-% glycerin ether ethoxylates. In addition, without being limited according to the invention, all ranges recited are inclusive of the numbers defining the range and include each integer within the defined range.

According to an embodiment of the invention, glycerin ether ethoxylate solfactants according to the following formula are provided in the sanitizing compositions:

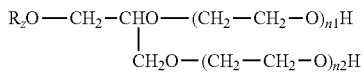

wherein $R_Z$ is $CH_3$, a combination $CH_3CH_2$, or a linear or branched alkyl group having 1 to 30 carbon atoms, preferably 4 to 25 carbon atoms, more preferably 6 to 18 carbon atoms, and wherein $n_1$ and/or $n_2$ is 1 to 25, preferably 1 to 20, preferably from 1 to 15. In an aspect of the invention n may vary between the ethoxylated tails of the solfactant, such that an average degree of ethoxylation (average EO) is between 1-25, preferably from 1 to 20, and more preferably from 1 to 9. Varying amounts of the ethylene oxide (EO or $C_2H_4O$) may be included in the glycerin ether ethoxylate solfactants.

The average molecular weight of the glycerin ether ethoxylate solfactants according to the invention is from about 200 to about 10,000, preferably from about 200 to about 5,000, more preferably from about 200 to about 3,000.

The glycerin ether ethoxylates have a hydrophobic head and twin EO hydrophilic tails providing unique properties. The novel surfactants have a twin tail or Gemini-like structure, as a result of the ethoxylation of the hydroxyl groups of the glycerin ether. The twin hydrophilic tails are distinct from conventional twin tail or Gemini surfactants due to the tails being hydrophilic and the single head being hydrophobic. As a result, the glycerin ether ethoxylate solfactants of the present invention are distinct from conventional alcohol ethoxylate surfactants due to the branched structure of the glycerin ether yielding a branched (i.e. twin), hydrophilic ethoxylated tails of the novel solfactants.

Beneficially, the glycerin ether ethoxylate solfactants are water soluble. In preferred aspects, the solfactants are 100% soluble, which as one skilled in the art will vary depending up on the degree of ethoxylation (e.g. moles of ethoxylation). In comparison to conventional alcohol ethoxylate surfactants, such as an alcohol ethoxylate with 3 moles of ethoxylation (such as commercially-available as Tomadol® 1-3), which are known to be water insoluble, the equivalent glycerin ether 3 mole ethoxylate solfactant is water soluble. An additional beneficial characteristic of the glycerin ether ethoxylate solfactants is the low melt points of the compositions, resulting in the solfactants being suitable for liquid formulations at low temperatures.

Additional suitable substitutions to the glycerin ether ethoxylates are set forth below describing variations in ethoxylation and/or propoxylation of the glycerin ethers. In an aspect of the invention, propylene oxide can be added to the glycerin ether ethoxylate of the invention. In some embodiments the water solubility can be adjusted based upon the inclusion of propoxylation of the glycerin ether ethoxylates, such as shown in exemplary EO/PO solfactants and/or PO solfactants.

In addition to the substitution to the glycerin ether ethoxylates using ethoxylation and/or propoxylation, the solfactants may further be modified by "capping" or "end blocking" the terminal ethoxylate group or groups. In an aspect, the propylene oxide group is a preferred cap. In other suitable aspects, the solfactant may have a halogen cap, including for example, fluorine (F), chlorine (Cl), bromine (Br), and iodine (I). In an aspect, the solfactant has a fluoro-, chloro-, bromo-, or iodo-cap. In other aspects, the cap may include linear, branched and/or aromatic hydrocarbons.

The glycerin ether ethoxylate solfactants according to the invention can have varying degrees of water solubility, which are not intended to limit the scope of the invention. In some aspects, the glycerin ether ethoxylate solfactants and/or propoxylate solfactants are water insoluble. In other aspects of the invention, the glycerin ether ethoxylates are slightly water soluble and/or substantially water soluble. In yet other aspects of the invention, the glycerin ether ethoxylates are completely water soluble. As one skilled in the art will ascertain, an increase in the degree of ethoxylation of the glycerin ether ethoxylates will increase the water solubility of the surfactants. Similarly, an increase in the degree of propoxylation will decrease the water solubility of the surfactants.

In a further aspect of the invention, the glycerin ether ethoxylates have additional improved properties, including for example, gel formation, foam production, hydrotroping, cleaning, pour and melt points and/or cloud points, in comparison to conventional alcohol ethoxylates, providing beneficial properties for product formulations.

In an aspect of the invention, the glycerin ether ethoxylate branches may disrupt gel formation and/or change the cloud points in comparison to conventional alcohol ethoxylates, providing beneficial properties for product formulations. In an aspect, the glycerin ether ethoxylate solfactants do not form a gel in solution with any concentration of water.

In some embodiments, the sanitizing compositions do not include alcohol ethoxylates in combination with the solfactants. However, in other embodiments, alcohol ethoxylates can be optionally included.

EO-PO/PO-EO/PO Glycerin Ether Solfactants

According to an additional embodiment of the invention, EO-PO glycerin ethers and/or PO glycerin ethers and/or PO-EO glycerin ethers are provided for use in compositions in need of a solfactant disclosed herein.

PO glycerin ethers according to the following formulas are provided:

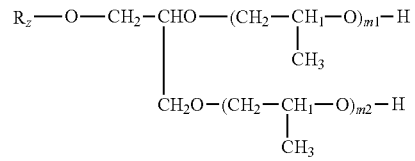

wherein $R_Z$ is $CH_3$, a combination $CH_3CH_2$, or a linear or branched alkyl group having 1 to 30 carbon atoms, preferably 4 to 25 carbon atoms, more preferably 6 to 18 carbon atoms, and wherein $m_1$ and/or $m_2$ is 1 to 25, preferably 1 to 20, preferably from 1 to 15. In an aspect of the invention m may vary between the propoxylated tails of the surfactant, such that an average degree of propoxylation (average PO) is between 1-25, preferably from 1 to 20, and more preferably from 1 to 9. Varying amounts of the propylene oxide (PO or $C_3H_6O$) may be included in the PO glycerin ethers.

The average molecular weight of the PO glycerin ethers according to the invention may vary between about 200 to about 20,000, preferably from about 200 to about 10,000, more preferably from about 200 to about 5,000.

In an additional aspect of the invention, EO-PO glycerin ethers according to the following formulas are provided:

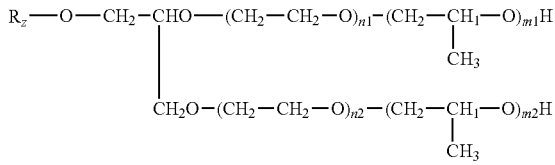

wherein $R_Z$ is $CH_3$, a combination $CH_3CH_2$, or a linear or branched alkyl group having 1 to 30 carbon atoms, preferably 4 to 20 carbon atoms, more preferably 6 to 18 carbon atoms, wherein $n_1$ and/or $n_2$ is 1 to 25, preferably 1 to 20, preferably from 1 to 15, and wherein $m_1$ and/or $m_2$ is 1 to 25, preferably 1 to 20, preferably from 1 to 15. In an aspect of the invention n and m may vary between the ethoxylated and propoxylated tails of the surfactant, such that an average degree of ethoxylation/propoxylation (average EO-PO) is between 1-30, preferably from 1 to 20, and more preferably from 1 to 9. Varying amounts of the ethylene oxide (EO or $C_2H_4O$) and propylene oxide (PO or $C_3H_6O$) may be included in the EO-PO glycerin ethers.

The average molecular weight of the EO-PO glycerin ethers according to the invention may vary between about 200 to about 40,000, preferably from about 200 to about 20,000, more preferably from about 200 to about 10,000.

In an additional aspect of the invention, PO-EO glycerin ethers according to the following formulas are provided:

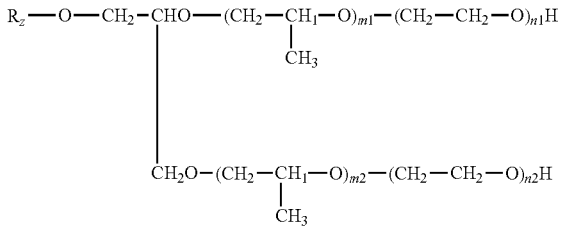

wherein $R_Z$ is $CH_3$, a combination $CH_3CH_2$, or a linear or branched alkyl group having 1 to 30 carbon atoms, preferably 4 to 20 carbon atoms, more preferably 6 to 18 carbon atoms, wherein $n_1$ and/or $n_2$ is 1 to 25, preferably 1 to 20, preferably from 1 to 15, and wherein $m_1$ and/or $m_2$ is 1 to 25, preferably 1 to 20, preferably from 1 to 15. In an aspect of the invention n and m may vary between the ethoxylated and propoxylated tails of the surfactant, such that an average degree of ethoxylation/propoxylation (average EO-PO) is between 1-30, preferably from 1 to 20, and more preferably from 1 to 9. Varying amounts of the ethylene oxide (EO or $C_2H_4O$) and propylene oxide (PO or $C_3H_6O$) may be included in the PO-EO glycerin ethers.

The average molecular weight of the PO-EO glycerin ethers according to the invention may vary between about 200 to about 40,000, preferably from about 200 to about 20,000, more preferably from about 200 to about 10,000.

Quaternary Ammonium Compounds

In an aspect, the compositions include from about 0.001 wt-%-60 wt-% cationic active ingredients containing quaternary ammonium groups, from about 0.01 wt-%-50 wt-% cationic active ingredients containing quaternary ammonium groups, from about 0.05 wt-%-40 wt-% cationic active ingredients containing quaternary ammonium groups, or more preferably from about 0.1 wt-%-30 wt-% cationic active ingredients containing quaternary ammonium groups. In addition, without being limited according to the invention, all ranges recited are inclusive of the numbers defining the range and include each integer within the defined range.

According to an aspect of the invention, cationic active ingredients containing quaternary ammonium groups are provided in the sanitizing compositions. The quaternary ammonium compounds are antimicrobial agents useful in the present invention in combination with the glycerin ether ethoxylates. The cationic or cationically-active ingredients are substances based on nitrogen centered cationic moieties with net positive change. The cationic or cationically-active ingredients are preferably selected from the group consisting of cationic polymers, cationic surfactants, cationic monomers, cationic silicon compounds, cationic derivatized protein hydrolyzates and betaine with at least one cationic or cationically-active group.

In an aspect, a blend of at least two of the cationic active ingredients containing quaternary ammonium groups are included in the sanitizing compositions.

Suitable cationic active ingredients contain quaternary ammonium groups. Suitable cationic active ingredients include those of the general formula:

which may also be depicted according to the following general formula:

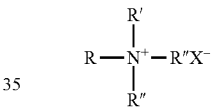

wherein $R^1$, $R^2$, $R^3$ and $R^4$ (formula 1; or R, R', R", R''' respectively for formula 2) independently of each other represent alkyl groups, aliphatic groups, aromatic groups, alkoxy groups, polyoxyalkylene groups, alkylamido groups, hydroxyalkyl groups, aryl groups, $H^+$ ions, each with from 1 to 22 carbon atoms, with the provision that at least one of the groups $R^1$, $R^2$, $R^3$ and $R^4$ has at least eight carbon atoms and wherein X(−) represents an anion, for example, a halogen, acetate, phosphate, nitrate or alkyl sulfate, preferably a chloride. The aliphatic groups can also contain cross-linking or other groups, for example additional amino groups, in addition to the carbon and hydrogen atoms. Additional description of quaternary ammonium groups is set forth, for example, in U.S. Pat. No. 8,221,733, which is herein incorporated by reference in its entirety. Suitable quaternary ammonium containing groups are often referred to as quaternary ammonium compound or quaternary ammonium cation compound, which are still further commonly referred to as a "quat." Exemplary quaternary ammonium compounds include, for example, alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof.

Exemplary alkylated quaternary ammonium compounds include ammonium compounds having an alkyl group containing between C6-C24. Exemplary alkylated quaternary ammonium compounds include monoalkyl trimethyl quaternary ammonium compounds, monomethyl trialkyl quaternary ammonium compounds, and dialkyl dimethyl quaternary ammonium compounds. The alkyl group can be a C8-C22 group or a C8-C18 group or a C12-C22 group that is aliphatic and saturated or unsaturated or straight or branched, an alkyl group, a benzyl group, an alkyl ether propyl group, hydrogenated-tallow group, coco group, stearyl group, palmityl group, and soya group. Further, exemplary ring or cyclic quaternary ammonium compounds include imidazolinium quaternary ammonium compounds, such as methyl-1hydr. tallow amido ethyl-2-hydr. tallow imidazolinium-methyl sulfate, methyl-1-tallow amido ethyl-2-tallow imidazolinium-methyl sulfate, methyl-1-oleyl amido ethyl-2-oleyl imidazolinium-methyl sulfate, and 1-ethylene bis(2-tallow, 1-methyl, imidazolinium-methyl sulfate).

Additional suitable cationic active ingredients include triamines having the general formula:

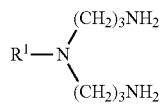

wherein $R^1$ is an alkyl group, in some aspects a C6-C18 alkyl group. Alkyl includes unbranched or branched alkyl groups of the specified number of carbons, but preferably unbranched alkyl groups, and particularly preferably those having an even number of carbon atoms.

Additional exemplary quaternary ammonium compounds include alkanolamines, which include all ethanolamines and propanolamines, in particular monoethanolamine, diethanolamine, triethanolamine and 3-amino-1-propanol. Alkanolamines have the following general structure:

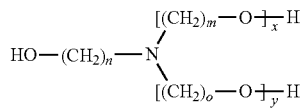

wherein where n and, if present, m and o independently of one another have the value 2 or 3, and x and y independently of one another have the value 0 or 1, or a corresponding salt. In an aspect, employing mixtures of the alkanolamines is also within the scope of embodiments of the invention.

Still further, exemplary aromatic quaternary ammonium compounds include those compounds that have at least one benzene ring in the structure. Exemplary aromatic quaternary ammonium compounds include dimethyl alkyl benzyl quaternary ammonium compounds, monomethyl dialkyl benzyl quaternary ammonium compounds, trimethyl benzyl quaternary ammonium compounds, and trialkyl benzyl quaternary ammonium compounds. Further, the alkyl group can contain between about 6 and about 24 carbon atoms, and can contain between about 10 and about 18 carbon atoms, and can be a stearyl group or a hydrogenated tallow group. Aromatic quaternary ammonium compounds can include multiple benzyl groups. Exemplary alkoxylated quaternary ammonium compounds include methyldialkoxy alkyl quaternary ammonium compounds, trialkoxy alkyl quaternary ammonium compounds, trialkoxy methyl quaternary ammonium compounds, dimethyl alkoxy alkyl quaternary ammonium compounds, and trimethyl alkoxy quaternary ammonium compounds. The alkyl group can contain between about C6-C24 and the alkoxy groups can contain between about 1 and about 50 alkoxy groups units wherein each alkoxy unit contains between about C2-C3. Exemplary amidoamine quaternary ammonium compounds may include methyl-bis(tallow amidoethyl)-2-hydroxyethyl ammonium methyl sulfate, methyl bis(oleylamidoethyl)-2-hydroxyethyl ammonium methyl sulfate, and methyl bis(hydrtallowamidoethyl)-2-hydroxyethyl ammonium methyl sulfate.

Additional cationic active ingredients particularly suitable for use in sanitizing compositions according to the invention include, for example, but are not limited to, alkyl dimethyl benzyl ammonium chloride, alkyl dimethyl ethyl benzyl ammonium chloride, dialkyl dimethyl ammonium chloride, octyl decyl dimethyl ammonium chloride, dioctyl dimethyl ammonium chloride, didecyl dimethyl ammonium chloride, benzethonium chloride, N,N-bis-(3-aminopropyl) dodecylamine, chlorhexidine gluconate, an organic and/or organic salt of chlorhexidene gluconate, PHMB (polyhexamethylene biguanide), salt of a biguanide, a substituted biguanide derivative, an organic salt of a quaternary ammonium containing compound or an inorganic salt of a quaternary ammonium containing compound or mixtures thereof.

The blend of at least two of the cationic active ingredients containing quaternary ammonium groups may be formulated to include additional inert ingredients, including for example water and other solvents. Organic compounds are particularly well suited for formulation with or without water, including for example ethyl alcohol.

Additional Functional Ingredients

The compositions of the invention may be suitable for use in a variety of cleaning compositions, including applications of use set forth in the methods of the invention. In an aspect of the invention, the compositions may be further formulated to include additional surfactants and/or additional functional ingredients (e.g. surfactants, additional sanitizing agents (e.g. alkanolamines), chelants and/or builders (e.g. chelant and/or remove water hardness to increase sanitizing performance of quaternary ammonium compound), solvents, sequestrants, antiredeposition agents, thickening agents, bleaching agents, fillers, defoaming agents, dispersants, dyes, fragrances, preservatives, other adjuvants, hydrotropes, water and the like), such as those described, for example, in U.S. Pat. No. 7,341,983, which is herein incorporated by reference. It should be understood by those of skill in the art and others that the particular materials are given by way of example only, and that a broad variety of other functional materials may be used. For example, many of the functional materials relate to materials used in cleaning applications, but it should be understood that other embodiments may include functional materials for use in other applications.

In an aspect, the compositions include from about 0 wt-%-40 wt-% additional functional ingredients, from about 0 wt-%-25 wt-% additional functional ingredients, from about 0 wt-%-20 wt-% additional functional ingredients, or more preferably from about 0 wt-%-15 wt-% additional functional ingredients. In addition, without being limited according to the invention, all ranges recited are inclusive of the numbers defining the range and include each integer within the defined range.

The compositions of the invention may be formulated into a variety of forms, including for example, microemulsions, solutions, solids and the like.

Compositions Employing Glycerin Ether Ethoxylate Solfactants

Beneficially, in an aspect of the invention, the solfactants provide a component that may replace and/or reduce the required amount of a solvent in a cleaning composition. Without being limited according to the theory of the invention, the solfactants disclosed herein provide combined efficacy as surfactants and solvents, providing enhanced soil removal properties and desirable a viscosity adjustments of the final compositions employing the solfactants, which vary according to the intended final use of the compositions.

For example, in some aspects of the invention, the solfactant replaces and/or reduces the amount of solvent employed in a cleaning composition. Such solvents may include, for example, isopropyl alcohol. Additional solvents which may be reduced and/or replaced with the solfactants according to the invention, include for example: oxygenated solvents such as lower alkanols, lower alkyl ethers, glycols, aryl glycol ethers, lower alkyl glycol ethers, methanol, ethanol, propanol, isopropanol, butanol, isobutanol, ethylene glycol, diethylene glycol, triethylene glycol, propylene glycol, dipropylene glycol, mixed ethylene-propylene glycol ethers, ethylene glycol phenyl ether, propylene glycol phenyl ether, propylene glycol methyl ether, propylene glycol propyl ether, dipropylene glycol methyl ether, tripropylene glycol methyl ether, ethylene glycol butyl ether, diethylene glycol methyl ether, diethylene glycol butyl ether, ethylene glycol dimethyl ether, ethylene glycol propyl ether, diethylene glycol ethyl ether, triethylene glycol methyl ether, triethylene glycol ethyl ether, triethylene glycol butyl ether and the like.

In some aspects, the present invention relates to sanitizing compositions including a quaternary ammonium containing compound or a salt thereof and a glycerin ether ethoxylate solfactant compound disclosed herein, or mixture thereof, having any of the following formulas:

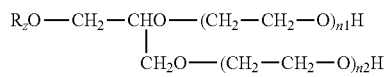

wherein $R_z$ is $CH_3$, a combination $CH_3CH_2$, or a linear or branched alkyl group having 1 to 30 carbon atoms, preferably 4 to 25 carbon atoms, more preferably 6 to 18 carbon atoms, and wherein n is 1 to 25, preferably 1 to 20, preferably from 1 to 15; or

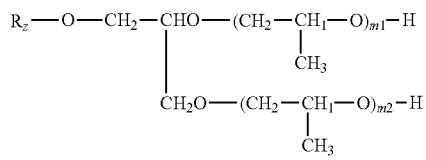

wherein $R_z$ is $CH_3$, a combination $CH_3CH_2$, or a linear or branched alkyl group having 1 to 30 carbon atoms, preferably 4 to 25 carbon atoms, more preferably 6 to 18 carbon atoms, and wherein $m_1$ and/or $m_2$ is 1 to 25, preferably 1 to 20, preferably from 1 to 15; or

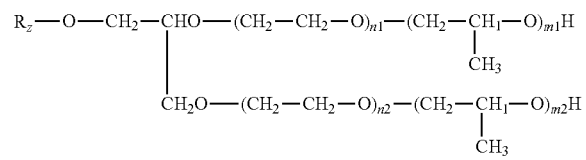

wherein $R_z$ is $CH_3$, a combination $CH_3CH_2$, or a linear or branched alkyl group having 1 to 30 carbon atoms, preferably 4 to 25 carbon atoms, more preferably 6 to 18 carbon atoms, wherein $n_1$ and/or $n_2$ is 1 to 25, preferably 1 to 20, preferably from 1 to 15, and wherein $m_1$ and/or $m_2$ is 1 to 25, preferably 1 to 20, preferably from 1 to 15; or

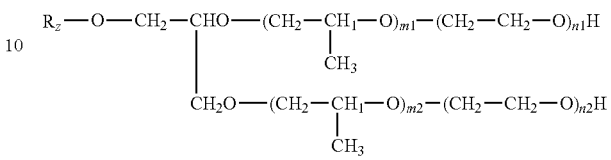

wherein $R_z$ is $CH_3$, a combination $CH_3CH_2$, or a linear or branched alkyl group having 1 to 30 carbon atoms, preferably 4 to 25 carbon atoms, more preferably 6 to 18 carbon atoms, wherein $n_1$ and/or $n_2$ is 1 to 25, preferably 1 to 20, preferably from 1 to 15, and wherein $m_1$ and/or $m_2$ is 1 to 25, preferably 1 to 20, preferably from 1 to 15.

The sanitizing compositions containing the solfactant compounds of the present invention can be used as antimicrobial and/or sanitizing compositions for a variety of substrates and surfaces, e.g., textiles, hard surfaces. The compositions of the present invention can also be used as disinfectant or antimicrobial compositions. Further, compounds of the present invention can be used as coupling agents in compositions for various applications, e.g., food contact sanitizing, hard surface disinfection, textile disinfection. In some embodiments, compositions containing compounds of the present invention can be multipurpose. That is, the compositions of the present invention can, for example, act as both antimicrobials and sanitizing agents, or as both coupling agents, and antimicrobial agents.

In an aspect, compositions employing the solfactant compounds of the present invention, including sanitizing compositions containing quaternary ammonium containing compound or a salt thereof, provide improved sanitizing efficacy in comparison to those compositions containing only a quaternary ammonium containing compound or a salt thereof. Moreover, the solfactant compounds despite being a suitable replacement for alcohol ethoxylates, alkoxylates, and/or propoxylates do not result in any diminished sanitizing performance as are known to skilled artisans.

In some embodiments, the compositions of the present invention include a glycerin ether ethoxylate solfactant compound or mixture thereof, quaternary ammonium containing compounds and/or salts thereof, and at least one additional ingredient. Additional ingredients suitable for use with the compositions of the present invention include, but are not limited to, oxidizing agents, carboxylic acids, surfactants, stabilizing agents (e.g., metal chelators), additional sanitizing agents, enzymes, dyes, odorants including perfumes, and other aesthetic enhancing agents, acidulants, alkalinity sources and mixtures thereof. The disclosed compositions may also contain additional typically non-active (e.g. inert) materials, with respect to cleaning and/or sanitizing properties. These ingredients are selected to be compatible with the materials of the invention and include such materials as fabric softeners, optical brighteners, soil suspension agents, germicides, viscosity modifiers, inorganic carriers, solidifying agents and the like.

In some embodiments, compositions employing the glycerin ether ethoxylate solfactant compounds of the present invention can be used as an antimicrobial and/or sanitizing composition for treatment of hard surfaces, skin, laundry, instruments and/or articles. Such compositions can include, for example, water (1-99 wt-%); Quaternary ammonium surfactant (0-50 wt-%); oxidizer (0-50 wt-%); anionic surfactant (0-40 wt-%); adjuvant ingredients (0-40 wt-%) and a glycerin ether ethoxylate solfactant (0.1-50 wt-%).

Various suitable oxidizing agents, carboxylic acids, stabilizing agents, wetting or defoaming agents, chelating agents; solvents and/or carriers, hydrotropes, acidulants, surfactants, additional functional materials, thickening or gelling agents, solidification agents, and/or mixture thereof, can be included within the exemplary formulations set forth herein. These components are described in further detail within, for example, U.S. Pat. Nos. 8,344,026, 8,216,989B2 and 7,341,983B2 and U.S. Patent Publication Nos. 2012/0052134, 2010/0048730, 2013/0035273A1 and 2012/0071438 which are herein incorporated by reference in their entirety.

In an aspect, the glycerin ether ethoxylates are suitable for formulation with any variety of surfactants, including, but not limited to, nonionic surfactants, anionic surfactants, cationic surfactants, amphoteric surfactants and/or zwitterionic surfactants.

Nonionic Surfactants

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp. Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Tetronic® compounds are tetra-flinctional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

2. Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol™ manufactured by Shell Chemical Co. and Alfonic™ manufactured by Vista Chemical Co.

4. Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol™ manufactured by Henkel Corporation and Lipopeg™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions of the present invention containing amylase and/or lipase enzymes because of potential incompatibility.

Examples of nonionic low foaming surfactants include:

5. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

6. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

7. The alkylphenoxypolyethoxyalkanols of U.S. Pat. No. 2,903,486 issued Sep. 8, 1959 to Brown et al. and represented by the formula

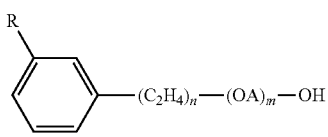

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n (C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O_n (C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n (C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

8. Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

9. The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

10. The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

11. Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

12. Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or —$(C_2H_4O)_xH$, where x is in the range of from 1 to 3.

13. A useful class of non-ionic surfactants include the class defined as alkoxylated amines or, most particularly, alcohol alkoxylated/aminated/alkoxylated surfactants. These non-ionic surfactants may be at least in part represented by the general formulae: $R^{20}$—$(PO)_sN$-$(EO)_tH$, $R^{20}$—$(PO)_sN$-$(EO)_tH(EO)_tH$, and $R^{20}$—$N(EO)_tH$; in which $R^{2o}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}$—$(PO)_v$—$N[(EO)_wH][(EO)_zH]$ in which $R^{2o}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic™ PEA 25 Amine Alkoxylate. Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface active agents are another class of nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

14. Amine oxides are tertiary amine oxides corresponding to the general formula:

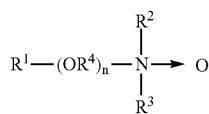

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

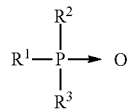

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

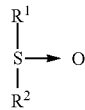

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, isododecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

Anionic Surfactants

Also useful in the present invention are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility. As those skilled in the art understand, anionics are excellent detersive surfactants and are therefore favored additions to heavy duty detergent compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R—O—(CH_2CH_2O)_n(CH_2)_m—CO_2X \quad (3)$$

in which R is a $C_8$ to $C_{22}$ alkyl group or

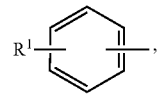

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

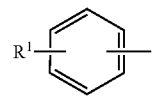

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Cationic Surfactants

Surface active substances are classified as cationic if the charge on the hydrotrope portion of the molecule is positive. Surfactants in which the hydrotrope carries no charge unless the pH is lowered close to neutrality or lower, but which are then cationic (e.g. alkyl amines), are also included in this group. In theory, cationic surfactants may be synthesized from any combination of elements containing an "onium" structure RnX+Y— and could include compounds other than nitrogen (ammonium) such as phosphorus (phosphonium) and sulfur (sulfonium). In practice, the cationic surfactant field is dominated by nitrogen containing compounds, probably because synthetic routes to nitrogenous cationics are simple and straightforward and give high yields of product, which can make them less expensive.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

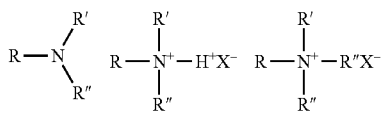

in which, R represents a long alkyl chain, R', R", and R'" may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", *Cosmetics & Toiletries*, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions of the present invention include those having the formula $R^1{}_m R^2{}_x Y_L Z$ wherein each $R^1$ is an organic group containing a straight or branched alkyl or alkenyl group optionally substituted with up to three phenyl or hydroxy groups and optionally interrupted by up to four of the following structures:

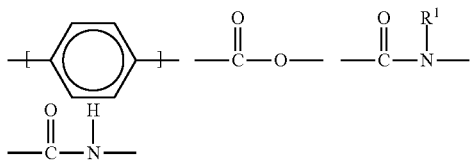

or an isomer or mixture of these structures, and which contains from about 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2 or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens. Y is can be a group including, but not limited to:

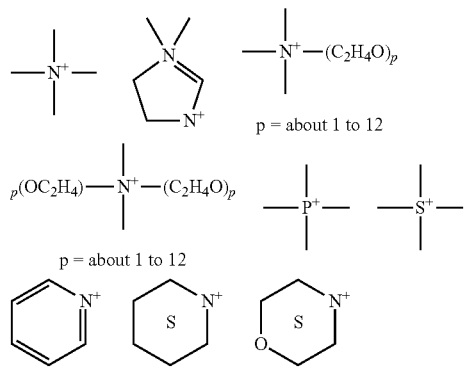

or a mixture thereof. Preferably, L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

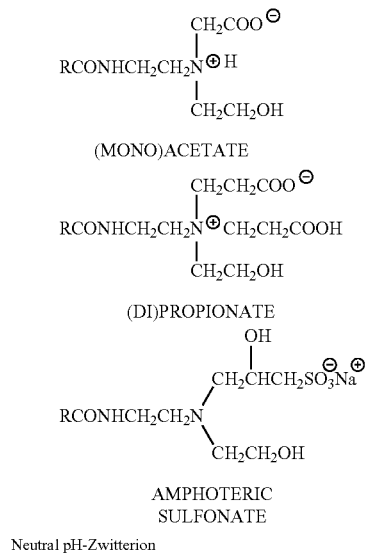

(MONO)ACETATE (DI)PROPIONATE

AMPHOTERIC SULFONATE

Neutral pH-Zwitterion wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na$)$_2$—$CH_2$—$CH_2$—OH or $C_{12}$-alkyl-C(O)—N(H)—$CH_2$—$CH_2$—$N^+$($CH_2$—$CO_2Na$)$_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated by reference in their entirety.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Betaine and sultaine surfactants are exemplary zwitterionic surfactants for use herein. A general formula for these compounds is:

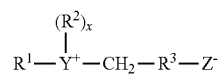

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N- hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

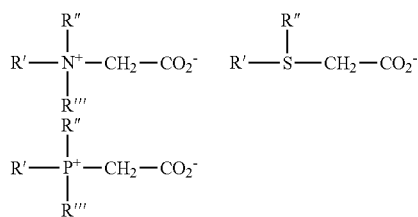

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

Methods of Use

The glycerin ether ethoxylate solfactants according to the present invention are well suited for use as substitutes and/or replacements for alcohol ethoxylate, alkoxylate, and/or propoxylate surfactants (in whole or in part), including for example, in the various compositions disclosed herein. From the disclosure herein, one skilled in the art will ascertain the glycerin ether ethoxylate solfactants can be used in any application, method or use wherein an alcohol ethoxylate is conventionally employed.

The glycerin ether ethoxylate solfactants according to the present invention are well suited for use as substitutes and/or replacements for solvents, solubilizers and/or hydrotropes (in whole in or part) in the various compositions disclosed herein. As one skilled in the art appreciates, "alcohol ethoxylates" include a variety of branched or linear ethoxylates that may be primary, secondary, or tertiary, and may further be nonionic or anionic. In an aspect of the invention, the compositions provide at least substantially similar cleaning performance, preferably improved cleaning performance, as alcohol ethoxylate surfactants. Similarly, the disclosure relating to alkoxylates and propoxylates shall include the same variety thereof.

Various methods of using the glycerin ether ethoxylate solfactants may be envisioned, including for example, applications for use in laundry and/or other textile cleaning, all-purpose cleaners and/or detergents, hard surface cleaners, disinfectants, sanitizers, sporicides and the like against a variety of microorganisms, use as rinse aids, lubricants, etc. In a further embodiment, methods of using the glycerin ether ethoxylates may include removing a plurality of soils from various surfaces, such as industrial surfaces, agricultural or veterinary surfaces, air streams, food processing surfaces, food products, meat products, poultry, health care surfaces, various instruments, plants, plant products, vehicles, ware, and the like.

The scope of the invention is not to be limited in any manner with respect to the methods of using the compositions.

Methods of employing the glycerin ether ethoxylate solfactants according to the invention employ varying amounts of actives of the composition, which will vary dependent upon the formulation of the composition, such as for example a concentrate composition as compared to a use solution.

In a further aspect, the methods of employing the glycerin ether ethoxylate solfactants (and compositions including the same) may include the use of concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the glycerin ether ethoxylate solfactant compound. Generally, a dilution of about 1 fluid ounce to about 10 gallons of water to about 10 fluid ounces to about 1 gallon of water is used for aqueous compositions of the present invention. In some embodiments, higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In some embodiments, when used in a laundry application, the concentrated compositions can be diluted at a dilution ratio of about 0.1 g/L to about 100 g/L concentrate to diluent, about 0.5 g/L to about 100 g/L concentrate to diluent, about 1.0 g/L to about 4.0 g/L concentrate to diluent, or about 1.0 g/L to about 2.0 g/L concentrate to diluent.

In other embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent.

In some embodiments, the methods of use employ the glycerin ether ethoxylate solfactant compound in an antimicrobial and/or sanitizing application of use. For example, the invention includes a method for reducing a microbial population and/or a method for sanitizing. These methods can operate on an article, surface, instrument, in a body or stream of water or a gas, or the like, by contacting the article, surface, instrument, body, or stream with a glycerin ether ethoxylate solfactant compound or composition of the invention. Contacting can include any of numerous methods for applying a compound or composition of the invention, such as spraying the compounds or compositions, immersing the article in the compounds or compositions, foam or gel treating the article with the compounds or composition, or a combination thereof.

In some aspects, a composition of the present invention includes an amount of the glycerin ether ethoxylate solfactant compound of the present invention effective for killing one or more of the food-borne pathogenic bacteria associated with a food product, including, but not limited to, *Salmonella typhimurium, Salmonella javiana, Campylobacter jejuni, Listeria monocytogenes*, and *Escherichia coli* 0157:H7, yeast, and mold. In some embodiments, the compositions of the present invention include an amount of glycerin ether ethoxylate solfactant compound effective for killing one or more of the pathogenic bacteria associated with a health care surfaces and environments including, but not limited to, *Salmonella typhimurium, Staphylococcus aureus*, methicillin resistant *Staphylococcus aureus, Salmonella choleraesurus, Pseudomonas aeruginosa, Escherichia coli*, mycobacteria, yeast, and mold. The compounds and compositions of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compounds and compositions of the present invention, as described above, have activity against a wide variety of human pathogens. The present compounds and compositions can kill a wide variety of microorganisms on a food processing surface, on the surface of a food product, in water used for washing or processing of food product, on a health care surface, or in a health care environment.

The compounds of the invention can be used for a variety of domestic or industrial applications, e.g., to reduce microbial or viral populations on a surface or object or in a body or stream of water. The compounds can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compounds of the invention can also be applied to soft surfaces such as food and skin (e.g., a hand). The present compounds can be employed as a foaming or nonfoaming environmental sanitizer or disinfectant.

The compounds and compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compounds can also be used in veterinary products such as mammalian skin treatments or in products for sanitizing or disinfecting animal enclosures, pens, watering stations, and veterinary treatment areas such as inspection tables and operation rooms. The present compounds can be employed in an antimicrobial foot bath for livestock or people. The compounds of the present invention can also be employed as an antimicrobial teat dip.

In some aspects, the compounds of the present invention can be employed for reducing the population of pathogenic microorganisms, such as pathogens of humans, animals, and the like. The compounds exhibit activity against pathogens including fungi, molds, bacteria, spores, and viruses, for example, *S. aureus, E. coli*, Streptococci, *Legionella, Pseudomonas aeruginosa*, mycobacteria, tuberculosis, phages, or the like. Such pathogens can cause a variety of diseases and disorders, including mastitis or other mammalian milking diseases, tuberculosis, and the like. The compounds of the present invention can reduce the population of microorganisms on skin or other external or mucosal surfaces of an animal. In addition, the present compounds can kill pathogenic microorganisms that spread through transfer by water, air, or a surface substrate. The compounds need only be applied to the skin, other external or mucosal surfaces of an animal water, air, or surface.

The antimicrobial compounds can also be used on foods and plant species to reduce surface microbial populations; used at manufacturing or processing sites handling such foods and plant species; or used to treat process waters around such sites. For example, the compounds can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compounds of the invention can be used to treat produce transport waters such as those found in flumes, pipe transports, cutters, slicers, blanchers, retort systems, washers, and the like. Particular foodstuffs that can be treated with compounds of the invention include eggs, meats, seeds, leaves, fruits and vegetables. Particular plant surfaces include both harvested and growing leaves, roots, seeds, skins or shells, stems, stalks, tubers, corms, fruit, and the like. The compounds may also be used to treat animal carcasses to reduce both pathogenic and non-pathogenic microbial levels.

The antimicrobial compounds can also be used to treat waste water and/or other industrial water sources where both its antimicrobial function and its oxidant properties can be utilized. Aside from the microbial issues surrounding waste water, it is often rich in malodorous compounds of reduced sulfur, nitrogen or phosphorous. In some aspects, the invention includes methods of using the solfactant compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid compositions are used to control the growth of microorganisms in water used in various oil and gas operations. In a further aspect, the compositions are suitable for incorporating into fracturing fluids to control or eliminate microorganisms. For the various industrial processes disclosed herein, "liquid system"

refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In some aspects, the compounds and compositions of the present invention are useful in the cleaning or sanitizing of containers, processing facilities, or equipment in the food service or food processing industries. The compounds and compositions have particular value for use on food packaging materials and equipment, and especially for cold or hot aseptic packaging. Examples of process facilities in which the compound of the invention can be employed include a milk line dairy, a continuous brewing system, food processing lines such as pumpable food systems and beverage lines, etc. Food service wares can be disinfected with the compound of the invention. For example, the compounds can also be used on or in ware wash machines, low temperature ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash and low temperature ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compounds and compositions can also be used on or in other industrial equipment and in other industrial process streams such as heaters, cooling towers, boilers, retort waters, rinse waters, aseptic packaging wash waters, and the like. The compounds can be used to treat microbes and odors in recreational waters such as in pools, spas, recreational flumes and water slides, fountains, and the like.

A filter containing the compound can reduce the population of microorganisms in air and liquids. Such a filter can remove water and air-borne pathogens such as *Legionella*.

The present compounds can be employed for reducing the population of microbes, fruit flies, or other insect larva on a drain or other surface.

The compounds of the present invention can also be employed by dipping food processing equipment into the use solution, soaking the equipment for a time sufficient to sanitize the equipment, and wiping or draining excess solution off the equipment, The compound may be further employed by spraying or wiping food processing surfaces with the use solution, keeping the surfaces wet for a time sufficient to sanitize the surfaces, and removing excess solution by wiping, draining vertically, vacuuming, etc.

The compounds of the present invention may also be used in a method of sanitizing hard surfaces such as institutional type equipment, utensils, dishes, health care equipment or tools, and other hard surfaces.

The antimicrobial compounds can be applied to microbes or to soiled or cleaned surfaces using a variety of methods. These methods can operate on an object, surface, in a body or stream of water or a gas, or the like, by contacting the object, surface, body, or stream with a compound of the invention. Contacting can include any of numerous methods for applying a compound, such as spraying the compound, immersing the object in the compound, foam or gel treating the object with the compound, or a combination thereof.

Other hard surface cleaning applications for the compounds of the present invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include the internal components of tanks, lines, pumps and other process equipment used for processing typically liquid product streams such as beverages, milk, juices.

In some aspects, the present invention provides methods for contacting a food product with the glycerin ether ethoxylate solfactants or compositions containing the solfactants, employing any method or apparatus suitable for applying such a compound or composition. For example, in some embodiments, the food product is contacted by a compound of the present invention with a spray of the compound, by immersion in the compound, by foam or gel treating with the compound. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the compounds of the present invention to other objects.

In other aspects, the solfactant compounds of the present invention can be used in the manufacture of beverage, food, and pharmaceutical materials including fruit juice, dairy products, malt beverages, soybean-based products, yogurts, baby foods, bottled water products, teas, cough medicines, drugs, and soft drinks. The compounds of the present invention can be used to sanitize, disinfect, act as a sporicide for, or sterilize bottles, pumps, lines, tanks and mixing equipment used in the manufacture of such beverages. Further, the solfactant compounds of the present invention can be used in aseptic, cold filling operations in which the interior of the food, beverage, or pharmaceutical container is sanitized or sterilized prior to filling. In such operations, a container can be contacted with a sanitizing solfactant compound composition, typically using a spray, dipping, or filling device to intimately contact the inside of the container with the sulfoperoxycarboxylic acid compound, for a sufficient period of time to reduce microorganism populations within the container. The container can then be emptied of the amount of sanitizer or sterilant used. After emptying, the container can be rinsed with potable water or sterilized water and again emptied. After rinsing, the container can be filled with the beverage, food, or pharmaceutical. The container can then be sealed, capped or closed and then packed for shipment for ultimate sale. The sealed container can be autoclaved or retorted for added microorganism kill.

In some aspects, the compounds can also be employed in sanitizing articles, e.g., textiles, which have become contaminated. The articles are contacted with the compounds of the invention at use temperatures in the range of about 4° C. to 80° C., for a period of time effective to sanitize, disinfect, and/or sterilize the articles. In some embodiments, the compounds of the present invention can be used to bleach and/or sanitize articles at a temperature of about 30° C. to about 50° C. or about 40° C. For example, in some embodiments, the compounds of the present invention can be injected into the wash or rinse water of a laundry machine and contacted with contaminated fabric for a time sufficient to sanitize the fabric. In some embodiments, the contaminated fabric is contacted with the compounds and compositions of the present invention for about 5 to about 30 minutes. Excess solution can then be removed by rinsing or centrifuging the fabric.

The compounds and compositions of the present invention can be used alone to treat the articles, e.g., textiles, or can be used in conjunction with conventional detergents suitable for the articles to be treated. The compounds and compositions of the invention can be used with conventional detergents in a variety of ways, for example, the compounds and compositions of the invention can be formulated with a conventional detergent. In other embodiments, the compounds and compositions of the invention can be used to treat the article as a separate additive from a conventional detergent. When used as a separate additive, the compounds and compositions of the present invention can contact the article to be treated at any time. For example, the compounds and compositions of the invention can contact the article before, after, or substantially simultaneously as the articles are contacted with the selected detergent.

A concentrate or use concentration of a compound of the present invention can be applied to or brought into contact with an object by any conventional method or apparatus for applying an antimicrobial or cleaning compound to an object. For example, the object can be wiped with, sprayed with, foamed on, and/or immersed in the compound, or a use solution made from the compound. The compound can be sprayed, foamed, or wiped onto a surface; the compound can be caused to flow over the surface, or the surface can be dipped into the compound. Contacting can be manual or by machine. Food processing surfaces, food products, food processing or transport waters, and the like can be treated with liquid, foam, gel, aerosol, gas, wax, solid, or powdered stabilized compounds according to the invention, or solutions containing these compounds.

In some aspects, the compounds of the present invention can be employed for various non-cleaning compositions, including for example, paint formulations, glues, lubricants, coolant compositions, fiber glass sizing compositions, water treatment compositions, drilling fluids, gas hydrate inhibitor compositions, corrosion inhibitor compositions, personal care compositions and the like wherein the freezing and/or melting point properties of the solfactants are desired. The solfactant compounds exhibit beneficial properties of having no freezing and/or melting to very low temperatures, including for example to at least about minus 80° C. The compounds of the present invention can maintain liquid formulations at low temperatures without resulting in freezing.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Initial bench methods for making the glycerin ether ethoxylates of the invention used ethoxylation methods employing ethylene oxide (EO or $C_2H_4O$) to combine with an alcohol (—OH groups suitable for ethoxylation) on a glycerin ether to create the novel surfactant. Initial methods used potassium hydroxide (KOH) as an imitator for the catalytic reaction. Potassium hydroxide, ethylene oxide and a glycerin ether precursor were combined in a heated, pressurized reactor to produce a cationic alcohol capable of reacting with the ethylene oxide.

The glycerin ether precursor employed was glycidyl ether having the following structure:

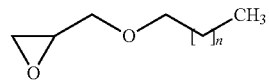

wherein n is 1 to 25, preferably n is 4 to 20, preferably n is 6 to 18, more preferably n is 10 to 12. The glycidyl ether was obtained from Sigma Aldrich and employed due to the limited commercial availability of larger chain glycerin ethers. The glycidyl ether (e.g. glycerin ether precursor) was converted to the corresponding glycerine ether via an acid catalyzed ring opening of the epoxide. The resulting mixture was then ethoxylated into the glycerin ether ethoxylates according to the invention.

NMR analysis was conducted on the glycerin ether ethoxylates produced according to Example 1. NMR confirms the presence of twin, ethoxylated hydrophilic tails along with the glycerin ether hydrophobic head of the surfactant as well as dimeric and oligomeric species.

Example 2

Various 2-Ethyl Hexanol Glycerin Ether Ethoxylate solfactants were produced using ethoxylation by a KOH Catalyst. The various physical and chemical properties of the exemplary set of novel solfactants are shown in Table 1.

TABLE 1

| Target EO | NMR Moles EO | Wt-% EO | Wt-% Free Alcohol | Wt-%PEG | % 2° Alc. Covered | Cloud Point Data 10% in BDG Soln. | 1% in D.I. H2O | 1% in 10% NaCl |
|---|---|---|---|---|---|---|---|---|
| 2EHGE (1 EO) | 1 | 17.7 | — | — | 30.4 | 59.5° C. | — | — |
| 2EHGE (3 EO) | 3.03 | 39.5 | 3.24 | — | 59.6 | — | 50.5° C. | 33° C. |
| 2EHGE (5 EO) | 5.07 | 52.2 | 0.24 | — | 76.7 | — | — | 71.5° C. |
| 2EHGE (7 EO) | 7 | 60.2 | 0.02 | — | 85.6 | — | — | 78° C. |
| 2EHGE (9 EO) | 8.98 | 66 | <0.01 | — | 92.2 | — | — | 95° C. |

As shown in Table 1, the glycerin ether ethoxylates are shown as having increased moles of ethylene oxide (e.g. 1, 3, 5, 7, 9) and corresponding decreased percentage of free alcohol as the degree of ethoxylation increases among the solfactants. As shown, as the moles ethylene oxide increase on the solfactants the percentage of the secondary alcohol that is covered by the EO increases to over 90% (at 9 EO solfactant).

Further the cloud point data for the solfactants in various solutions is shown. The cloud point temperatures show the temperature above which a surfactant-rich phase separates from an aqueous solution. There is a clear relationship between the cloud point and the average EO content of the glycerin ether ethoxylate; as the ethylene oxide content of the solfactant increases, the cloud point and water solubility increase. As the carbon number on the molecule increases, a greater number of moles of ethylene oxide are required to be added to the molecule to retain the same cloud point.

Example 3

2-Ethyl hexanol glycerin ether ethoxylate (2EHGE) solfactants according to the invention were analyzed in comparison to commercially-available Tomadol® ethoxylated alcohols in cleaning compositions prepared for testing red and black soils. The evaluated formulas are shown in Table 2. The Tomadol surfactants have the following structures: RO(CH$_2$CH$_2$O)$_n$H, wherein R is a hydrophobic portion obtained from a linear alcohol, n is the average moles of ethylene oxide per mole of alcohol. In addition, a commercially available cleaning composition Super Excellent Standard (NPE 9.50) (Ecolab Inc.) was also used as a comparison composition. The 2EHGE solfactant compositions were formulated to provide a direct replacement for the ethoxylated alcohol with the glycerin ether ethoxylate, wherein the same moles ethylene oxide were employed in the various formulations shown in FIG. 1.

TABLE 2

| Component | Tomadol wt-% | 2EHGE wt-% |
|---|---|---|
| Water | 72.1 | 72.1 |
| Phosphoric acid (75%) | 0.4 | 0.4 |
| Isopropanol (3.5%) | 3.5 | 3.5 |
| Tetrasodium EDTA (40%) | 6 | 6 |
| Ethoxylated alcohol | 18 | 0 |
| 2-Ethyl hexanol glycerin ether ethoxylate | 0 | 18 |

Red Soil Removal Test

A black soil including about 50 grams mineral spirits, about 5 grams mineral oil, about 5 grams motor oil, about 2.5 grams black pigment dispersion and about 37.5 grams bandy black clay was prepared.

A plurality of 3"×3" white vinyl tiles were soiled on the back, grooved side with approximately 0.75 grams of the black test soil using a 3" foam brush. The tiles were allowed to dry at room temperature overnight. The next day, the tiles were placed into a soaking tray containing about 200 grams of the cleaning composition for about 2 minutes. The soil removal test was conducted using a Precision Force Applicator (PFA), available from Precision Analytical Instruments, Inc., using a synthetic sponge. The sponge was pre-dampened with water with the excess water squeezed out and then saturated with about 50 grams of the test compositions.

The tiles were then placed into a PFA (described below) with the grain of the tiles parallel to the direction of sponge travel. The tiles were then scrubbed with about 2 pounds of pressure with the moistened synthetic sponge for 40 cycles, rotating the tiles 90 degrees every 10 cycles for a complete 360 degree rotation of the tiles. The tiles were then rinsed with city water and dried overnight at room temperature. The average percentage reflectance change of the black soil removal was calculated by the following equation:

$$\% \text{ Clean} = \frac{((\text{Reflectance of Cleaned tile}) - (\text{Reflectance of Soiled tile}))}{((\text{Reflectance of New tile}) - (\text{Reflectance of Soiled tile}))}$$

FIG. 1 shows a graph comparing the black soil cleaning efficacy of the various cleaning compositions containing the glycerin ether ethoxylate solfactants versus the equivalent ethoxylated alcohols (i.e. Tomadol). A further control composition of Super Excellent (with NPE 9.5) (Ecolab Inc.) was tested. The graphs show that the replacement glycerin ether ethoxylate solfactants provide at least substantially similar cleaning efficacy to the equivalent Tomadol-based cleaning compositions, illustrating the suitability of the solfactants for providing an effective replacement for the commercially-available ethoxylated alcohol surfactants.

Red Soil Removal Test

A red soil consisting of lard, oil, protein, and iron (III) oxide (for color) was prepared. About 30 grams of lard was combined with about 30 grams of corn oil, about 15 grams of whole powdered egg, and about 1.5 grams of $Fe_2O_3$.

The back, grooved sides of a plurality of 3"×3" white vinyl tiles were soiled with approximately 0.75 grams of the red soil using a 3" foam brush. The tiles were allowed to dry at room temperature overnight. It is believed that this incubation period allowed the bonds holding the triglycerides and proteins together in the soil to begin to crystallize and interlink. The next day, the tiles were placed into a soaking tray containing about 200 grams of a test composition for about 1 minute.

The soil removal test was conducted using a Precision Force Applicator (PFA), available from Precision Analytical Instruments, Inc., using a synthetic sponge. The PFA is similar to the Gardner Straightline Apparatus except that it is interfaced with a computer to control various parameters, such as, for example speed, number of repetitions, time between cycles, etc. The synthetic sponge was pre-dampened with water with the excess water squeezed out and then saturated with about 50 grams of the test compositions. The tiles were then placed into the PFA with the grain of the tiles parallel to the direction of sponge travel. The tiles were scrubbed with about 2 pounds of pressure with the moistened synthetic sponge for 16 cycles, rotating the tiles 90 degrees every 4 cycles for a complete 360 degree rotation of the tiles. The tiles were then rinsed with city water and dried overnight at room temperature. Hunter Lab L* reflectance of the soiled tiles and washed tiles were measured. The soiled tiles L* reflectance value is represented by the following equation:

$$\text{soiled } L'^* = \frac{1}{3.38 \ln\left(\frac{92.1 - 24.74}{\text{soiled } L^* - 24.74}\right)}$$

where 3.38, 92.1, and 24.74 are constants. The washed tiles L* reflectance value is represented by the following equation:

$$\text{washed } L'^* = \frac{1}{3.38 \ln\left(\frac{92.1 - 24.74}{\text{washed } L^* - 24.74}\right)}$$

The percent soil removal was then calculated as:

$$\text{percent soil removal} = \left(\frac{\text{soiled } L'^* - \text{washed } L'^*}{\text{soiled } L'^*}\right) * 100$$

The compositions were evaluated based on two standards. First, the compositions were evaluated to determine whether an acceptable amount of red soil was removed at low concentrations (i.e., 4 oz./gallon), intermediate concentrations (i.e., 8 oz./gallon) and high concentrations (i.e., 16 oz./gallon). At 18% actives, a composition was considered to perform at an acceptable level if it removed at least about 71% red soil at low concentrations, at least about 79% red soil at intermediate concentrations and at least about 86% red soil at high concentrations.

Figure 2:
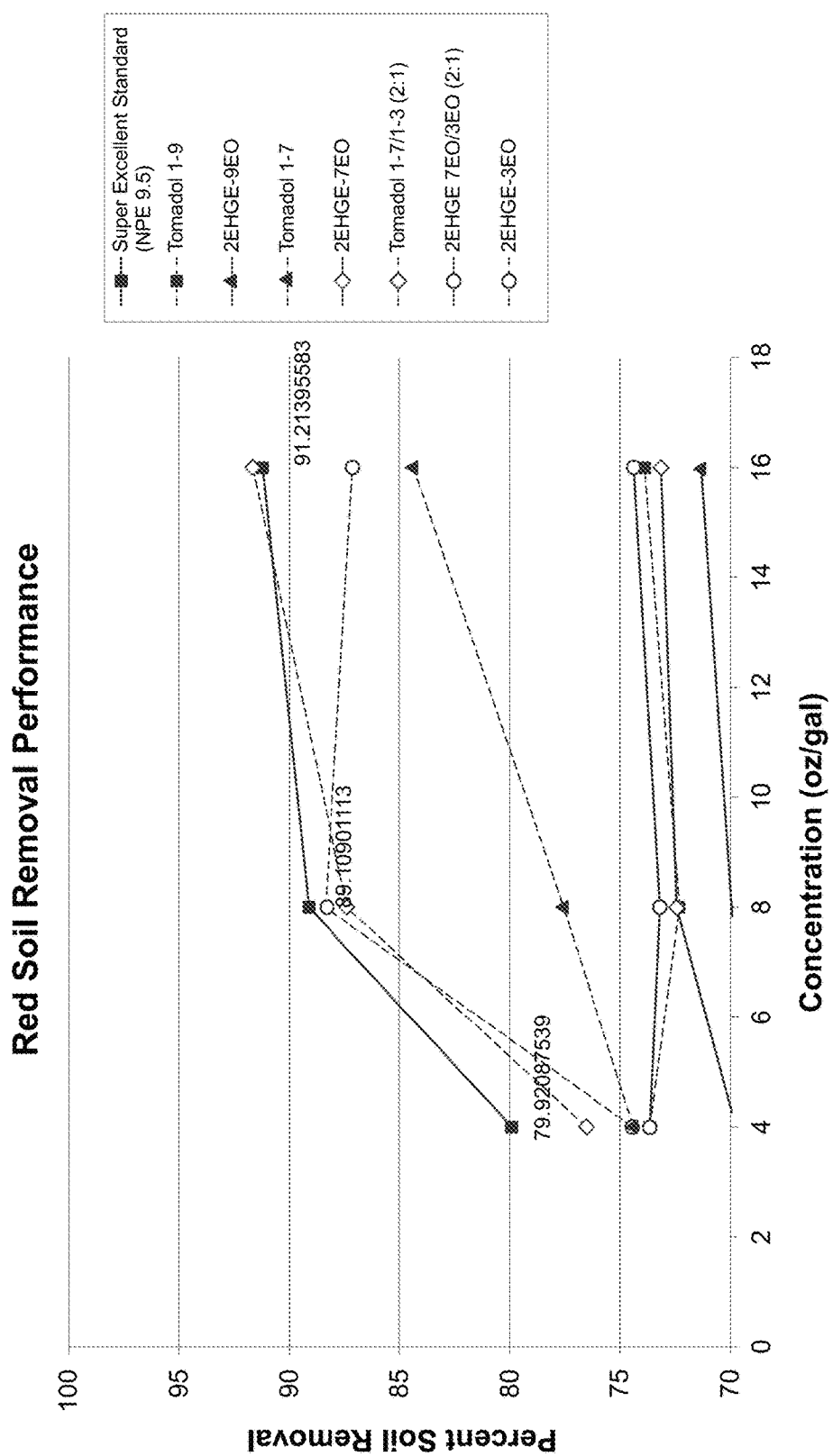
FIG. 2 shows a graph of various cleaning compositions containing the glycerin ether ethoxylate solfactants according to the invention, in comparison to a control composition (Super Excellent (with NPE 9.5)) and various equivalent ethoxylated alcohol based compositions on cleaning of red food soils.

FIG. 2 shows a graph comparing the red soil cleaning efficacy of the various cleaning compositions containing the glycerin ether ethoxylate solfactants versus the equivalent ethoxylated alcohols (i.e. Tomadol). A further control composition of Super Excellent (with NPE 9.5) (Ecolab Inc.) was tested. The graphs show that the replacement glycerin ether ethoxylate solfactants provide at least substantially similar cleaning efficacy to the equivalent Tomadol-based cleaning compositions, illustrating the suitability of the solfactants for providing an effective replacement for the commercially-available ethoxylated alcohol surfactants.

Example 4

Foam testing was completed for the ethoxylated glycerine ether solfactants in comparison to commercially-available ethoxylated alcohols using a Glewwe foam meter. A Glewwe foam meter provides a dynamic foam test rather than a static test, which is considered more appropriate for simulation of industrial conditions. The equipment and general procedure for the Glewwe form test is described in U.S. Pat. Nos. 3,899,387 and 5,447,648, which are herein incorporated by reference in its entirety. The foam meter itself consists of a thermostated reservoir and a pump to recirculate the aqueous medium with foaming tendencies. The foam developed by the action of the aqueous stream impinging on the surface in the reservoir causes foam formation.

The foam heights of the tested compositions were determined using the following method. First 3000 mL of city water (e.g. 17 gpg) was filled into the Glewwe cylinder. The pump was turned on, pressure adjusted to 6 psi, and heated water to 140° F. The commercially available surfactant (or the solfactant according to the invention) was added at 50 ppm in the cylinder and the timer was started. Foam height was recorded at 1 minute and 5 minutes. After 5 minutes the pump was stopped and foam stability characteristics were observed. The cylinder was then drained, rinsed, and the methods repeated. The results are shown in Table 3.

TABLE 3

| Surfactant | Conc. | Foam Height (in) @ 1 MIN | Foam Height (in) @ 5 MIN | OBSERVATIONS |
|---|---|---|---|---|
| Tomadol 1-3 | 50 ppm | 2.5 | 3.25 | Fast to break - remained fairly stable @ 1" |
| Tomadol 1-5 | 50 ppm | 9.5 | 9.5 | Very stable |
| Tomadol 1-7 | 50 ppm | 10 | 12 | Very stable |
| Tomadol 1-9 | 50 ppm | 10 | 12 | Very stable |
| Solfactant (1 mole EO) | 50 ppm | 3 | 3 | Unstable - Breaks quickly to 0" |
| Solfactant (3 mole EO) | 50 ppm | 3.5 | 4 | Unstable - Breaks quickly to 0" |
| Solfactant (5 mole EO) | 50 ppm | 4 | 4 | Unstable - Breaks quickly to 0" |
| Solfactant (7 mole EO) | 50 ppm | 5 | 4.5 | Unstable - Breaks quickly to 0" |
| Solfactant (9 mole EO) | 50 ppm | 4.5 | 4.5 | Unstable - Breaks quickly to 0" |

Results: As shown in Table 3 the glycerin ether ethoxylate solfactants according to the invention beneficially do not create high foam, which providing at least substantially similar cleaning performance. The low foam of the solfactants is illustrated in the "observations" wherein the foam height is "unstable" and quickly breaks down to no foam height. In various applications of use, such as for example, laundry and ware wash applications, low or no foaming cleaning compositions are desired. Beneficially, the ethoxylated glycerine ether solfactants generated significantly less foam in comparison to the Tomadol 1-X series ethoxylated alcohol surfactants.

Example 5

In addition to the low-foaming benefits of the glycerin ether ethoxylate solfactants, the compounds further provide lower viscosity in comparison to ethoxylated alcohol surfactants. The comparative viscosity of textile/laundry cleaning compositions shown in Table 4 was analyzed.

TABLE 4

| Component | Tomadol Formulation (wt-%) | Solfactant Formulation (wt-%) |
|---|---|---|
| Water | 59.8340 | 59.8340 |
| Tomadol 24-7 | 21.0000 | 0 |
| Tomadol 24-5 | 7.0000 | 0 |
| 2 ethylhexyl glycerin ether (7 moles) | 0 | 21.0000 |
| 2 ethylhexyl glycerin ether (5 moles) | 0 | 7.0000 |
| Distyryl biphenyl | 0.0160 | 0.0160 |
| Propylene Glycol | 12.0000 | 12.0000 |
| Chloro Methyl Isothiazolin | 0.1500 | 0.1500 |

Viscosity measurements for the Tomadol formulation and the Solfactant (2 ethylhexyl glycerin ether) formulation were conducted using a Brookfield Viscometer to measure the fluid friction resulting when a layer of fluid is moved in relation to another layer (measured in Poises). The Brookfield Viscometer measures viscosity by measuring the force required to rotate a spindle in a fluid according to known methods (Viscosity—Brookfield, TP-AATM-105A-b, 2006 Edition).

The viscometer was set and read at a constant reading to obtain the speed of the spindle (#3) in centipoises. To obtain the centipoise measurements from the evaluated formulas the propylene glycol (e.g. solvent) was removed and water wash added back in to total 100 wt-%. The Tomadol Formulation measured at 438 cps, whereas the Solfactant measured at 5 cps. The viscosity of the solfactant was similar to water having minimal measurable viscosity. However, the viscosity of the Tomadol Formulation was unpourable These results demonstrate the unexpected solvent-type benefits provided by the glycerin ether ethoxylate solfactants, including the 2 ethylhexyl glycerin ether ethoxylate solfactant. The solfactant demonstrates its suitable use for forming more concentrated formulations without having substantial increases in viscosity. This attribute of the solfactant is critical to maintain a highly concentrated formulation that is pourable and/or flowable.

Example 6

The low foam profiles and low viscosity of the glycerin ether ethoxylate solfactants as shown in Examples 5 and 6 were further compared to gel curves of conventional ethoxylated alcohols (e.g. Tomadol surfactants). The glycerin ether ethoxylate solfactant 2 ethylhexyl glycerin ether (having various moles ethylene oxide) was evaluated as shown in Table 5 to determine at what concentrations a gel would form with water.

TABLE 5

| Solfactant | Glycerin Ether Ethoxylate %/Water % | Gel Formation |
|---|---|---|
| 2 ethylhexyl glycerin ether (3 moles) | 10%/90% | None |
| | 20%/80% | None |
| | 30%/70% | None |
| | 40%/60% | None |
| | 50%/50% | None |
| | 60%/40% | None |
| | 70%/30% | None |
| | 80%/20% | None |
| | 90%/10% | None |
| 2 ethylhexyl glycerin ether (5 moles) | 10%/90% | None |
| | 20%/80% | None |
| | 30%/70% | None |
| | 40%/60% | None |
| | 50%/50% | None |
| | 60%/40% | None |
| | 70%/30% | None |
| | 80%/20% | None |
| | 90%/10% | None |
| 2 ethylhexyl glycerin ether (7 moles) | 10%/90% | None |
| | 20%/80% | None |
| | 30%/70% | None |
| | 40%/60% | None |
| | 50%/50% | None |
| | 60%/40% | None |
| | 70%/30% | None |
| | 80%/20% | None |
| | 90%/10% | None |
| 2 ethylhexyl glycerin ether (9 moles) | 10%/90% | None |
| | 20%/80% | None |
| | 30%/70% | None |
| | 40%/60% | None |
| | 50%/50% | None |
| | 60%/40% | None |
| | 70%/30% | None |
| | 80%/20% | None |
| | 90%/10% | None |

Figure 3A:
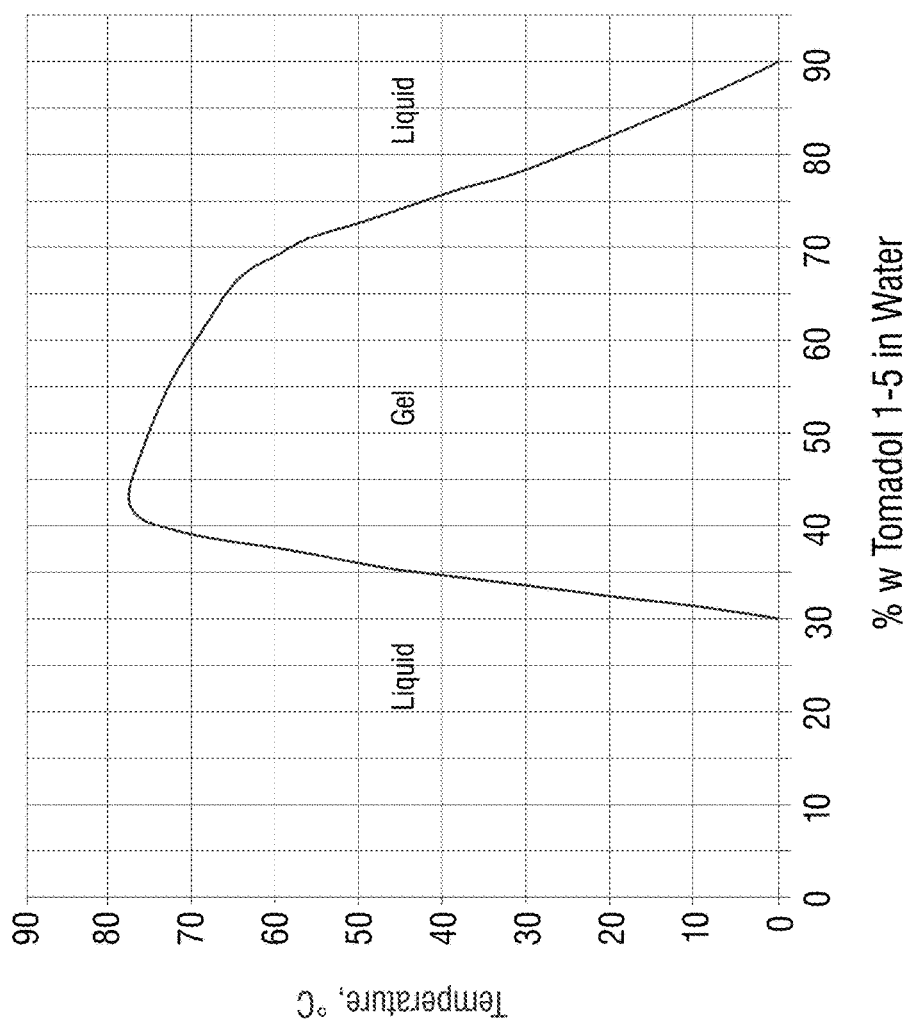
FIGS. 3A-3C show comparative graphs of gel curves of commercially-available ethoxylated alcohols for which the solfactants according to embodiments of the invention are suitable replacements or substitutes, and which do not form gels with any concentrations of water.
Figure 3B:
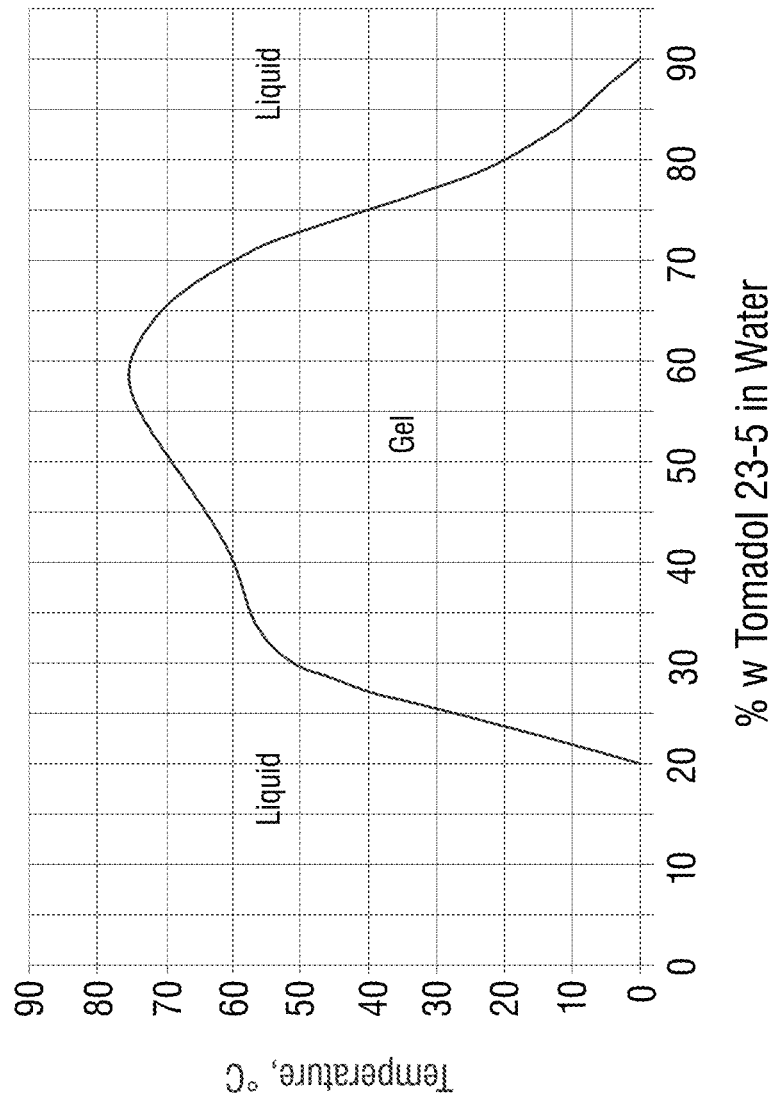
Figure 3C:
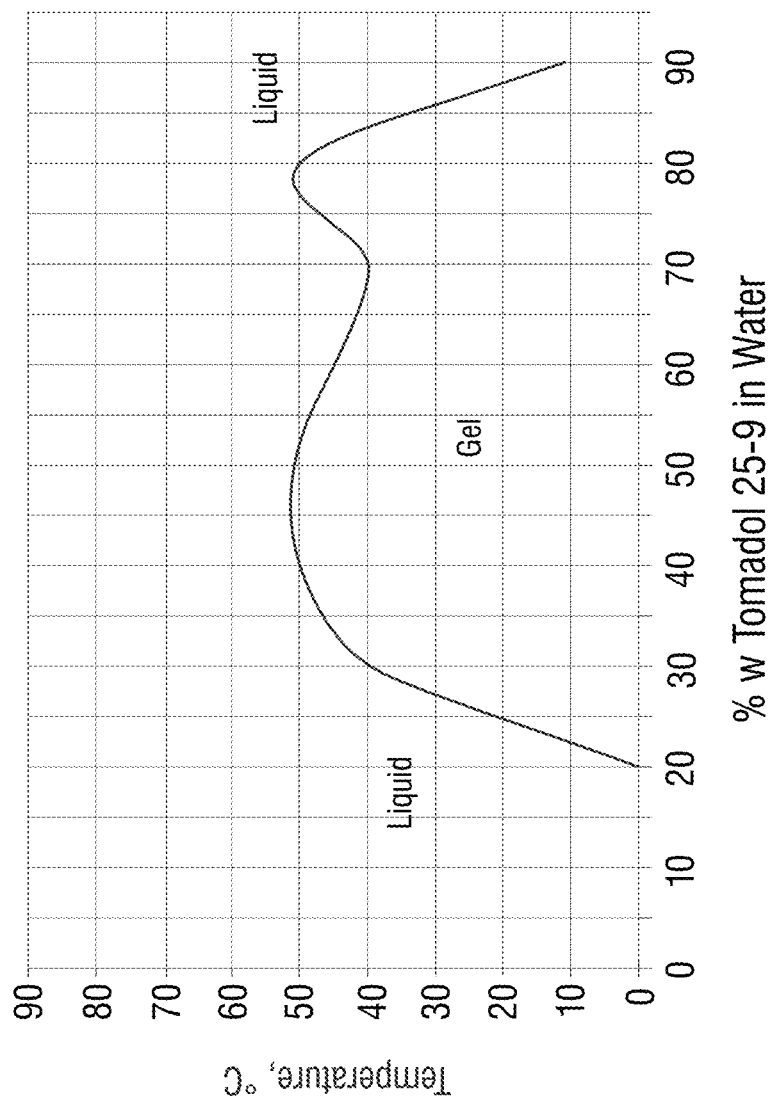

As shown in Table 5, regardless of the ratio of the solfactant and water there is no formation of a gel. This is a significant difference from the commercially-available ethoxylated alcohol surfactants (Tomadol series) that are shown in exemplary FIGS. 3A-3C showing graphs of the gel curves for the surfactants: Tomadol 1-5 (FIG. 3A), Tomadol 23-5 (FIG. 3B), Tomadol 25-9 (FIG. 3C). The gel curves indicate the temperatures over which the surfactants form gels and the corresponding concentration ranges that form gels.

The gel curves shown in FIGS. 3A-3C represent a significant from the glycerin ether ethoxylate solfactants according to the invention, which do not form gels under any of the concentrations with water, as set forth about in Table 5.

Example 7

The glycerin ether ethoxylate solfactants were evaluated for formulation and efficacy in a wide variety of cleaning compositions and applications, including for example: Dishwashing/Ware wash detergents, Auto dish detergents, Rinse additives, Manual detergents, Hand Soaps, Air Fresheners, Laundry (e.g. textile) detergents, Industry Water Treatments, Cosmetics, Disinfectants, Degreasers, Hard surface Cleaners and/or Solubilizers, Sanitizers, Stain Removers, Floor Cleaners, Auto floor scrubbers, CIP detergents, Teat dips, Bowl cleaners (e.g. toilet bowel cleaners), etc.

Suitable, non-limiting formulations for the various exemplary glycerin ether ethoxylate solfactant compositions according to the invention are set forth below in Tables 6-8.

TABLE 6

Degreaser Composition

| Component | Solfactant Formula wt-% | Surfactant Formula wt-% |
|---|---|---|
| Propylene glycol Phenyl Ether | 14.0000 | 14.0000 |
| Dowanol DPNB | 14.0000 | 14.0000 |
| Monoisopropanolamine | 12.0000 | 12.0000 |
| Tall Oil Fatty Acid | 10.0000 | 10.0000 |
| Benzoic Acid | 2.0000 | 2.0000 |
| Tomadol 1-3 | 0 | 4.0000 |
| Neodol 1-9 | 0 | 3.0000 |
| 2 ethylhexyl glycerin ether (3 moles) | 4.0000 | 0 |
| 2 ethylhexyl glycerin ether (9 moles) | 3.0000 | 0 |
| Versene 100 | 2.0000 | 2.0000 |
| SXS 40% | 3.0000 | 3.0000 |
| Water | 35.4880 | 35.4880 |
| Red Dye | 0.0120 | 0.0120 |
| Citrus Frag. | 0.5000 | 0.5000 |
|  | 100 | 100 |

The exemplary, non-limiting solfactant degreaser composition shown in Table 6 was formulated with a direct replacement of the conventional ethoxylated alcohol surfactants with the glycerin ether ethoxylate solfactants according to the invention. Beneficially, the solfactant compositions provide at least substantially similar cleaning efficacy while providing low foam, low viscosity compositions that can be concentrated at levels exceeding the conventional ethoxylated alcohol surfactant compositions.

TABLE 7

Hard Surface Cleaning/Solubilizer Composition

| Component | Solfactant Formula wt-% | Surfactant Formula wt-% |
|---|---|---|
| Water | 80.1670 | 79.6670 |
| MgCl2 | 2.2500 | 2.2500 |

TABLE 7-continued

Hard Surface Cleaning/Solubilizer Composition

| Component | Solfactant Formula wt-% | Surfactant Formula wt-% |
|---|---|---|
| LAS | 7.4400 | 7.4400 |
| TEA | 1.2400 | 1.2400 |
| NaOH | 1.5000 | 1.5000 |
| SLES | 3.5300 | 3.5300 |
| Tomadol 1-5 | 0.4600 | 0.4600 |
| Ethylan HB4 | 0 | 2.5000 |
| 2 ethylhexyl glycerin ether (9 moles) | 2.0000 | 0 |
| D-limonene | 1.2500 | 1.2500 |
| Dye | 0.0830 | 0.0830 |
| Kathon | 0.0800 | 0.0800 |
|  | 100 | 100 |

The exemplary, non-limiting solfactant hard surface cleaning/solubilizing composition shown in Table 7 was formulated using the solfactant as a replacement for the conventional solvent material Ethylan HB4. Notably, due to the solvent-based characteristics of the solfactants according to the invention, the glycerin ether ethoxylate solfactants replaced the solvent at a decreased concentration. Without being limited to a particular benefit and/or theory of the invention, the solvent-based characteristics of the glycerin ether ethoxylate solfactants allows for the more efficient formulation and interaction as both a solvent and a hydrotrope. In this exemplary formulation, the solfactant easily brings the water insoluble solvent (e.g. D-limonene) into solution using a lower concentration that the conventional solvent Ethylan HB4. Still further, the solfactant compositions provide at least substantially similar cleaning efficacy as the conventional ethoxylated alcohol surfactant compositions.

TABLE 8

Laundry Detergent Composition

| Component | Solfactant Formula wt-% | Surfactant Formula wt-% |
|---|---|---|
| Water | 68.5715 | 68.5715 |
| EDTA 40% | 3.0000 | 3.0000 |
| Sod. LAS | 9.2000 | 9.2000 |
| Cocamidopropyl Betaine | 1.2500 | 1.2500 |
| Coco DEA | 0.0500 | 0.0500 |
| SXS 40% | 6.8000 | 6.8000 |
| Ethylene Glycol Butyl ether | 6.0000 | 6.0000 |
| Lauryl Dimethylamine Oxide 30% | 1.3700 | 1.3700 |
| Alcohol Ethoxylate C9-11 (6 EO) | 0 | 0.9200 |
| Alcohol Ethoxylate C12-16 (7 EO) | 0 | 0.4600 |
| 2 ethylhexyl glycerin ether (5 moles) | 0.9200 | 0 |
| 2 ethylhexyl glycerin ether (7 moles) | 0.4600 | 0 |
| D'Limonene | 1.2000 | 1.2000 |
| MEA | 1.0000 | 1.0000 |
| Water | 0.1755 | 0.1755 |
| Dye, Turquoise XB CDG | 0.0030 | 0.0030 |
|  | 100.0000 | 100.0000 |

The exemplary, non-limiting solfactant laundry detergent composition shown in Table 8 was formulated using the solfactant as a replacement for the conventional alcohol ethoxylate surfactants. The solfactant compositions provide at least substantially similar cleaning efficacy as the conventional ethoxylated alcohol surfactant compositions, which is further illustrated in Example.

Example 8

Laundry detergent compositions using 500 ppm sodium hydroxide (e.g. caustic) and the indicated conventional Surfonic® surfactant or the glycerin ether ethoxylate solfactant according to the invention were evaluated. A tergotometer test procedure was employed to measure detergency of test compositions according to the invention. A tergotometer along with 500 mL pots and water bath were employed. First, unwashed swatches from the lot numbers to be used in the test are read on the Konica Minolta Spectrophotometer model CM-3600d to establish the average initial (before washing) L value. A sampling of each swatch type is used. The desired wash temperature is programmed into the Tergotometer and its water bath is allowed to heat up to that temperature. 500 mL of the desired water type is added to each Tergotometer pot and allowed to equilibrate to the desired temperature.

The following standard, commercially available (EMPA) soiled swatches were used for baseline testing in the Examples, as shown in Table 9.

TABLE 9

| Sample | Soil | Substrate Fabric |
|---|---|---|
| EMPA 101 | olive oil/carbon black | Cotton |
| EMPA 104 | olive oil/carbon black | Cotton blend |
| EMPA 106 | mineral oil | Cotton |

TABLE 9-continued

| Sample | Soil | Substrate Fabric |
|---|---|---|
| EMPA 111 | Pig blood | Cotton |
| EMPA 114 | Red wine | Cotton |
| EMPA 116 | Blood, milk and ink | Cotton |

The test detergent compositions are weighed out and added to the Tergotometer pots. Various detergent compositions as shown in Tables 10-11 were employed under varying water conditions, including 5 grain water (Table 10) and 17 grain water (Table 11).

The detergent systems were agitated for 10 minutes to mix and dissolve in the water sources. The agitation/mixing speed RPM was adjusted to 200. The temperature of the detergent compositions dissolved in water was 60° C., unless indicated otherwise in the Figures/Examples set forth below. The swatches are added quickly to their respective pots in a left to right sequence in order to minimize differences in exposure time to the detergent systems. A wash run is completed for at least 10 minutes. At the end of the run, the swatches are removed from the pots quickly in a left to right sequence using a forceps and are transferred into 500 mL-1 liter of cool water to rinse. After rinsing with cold tap water, excess water from the swatches was removed by squeezing the swatches. The process was repeated with rinsing and squeezing excess water at least 2 more times. The swatches were air dried on a visa napkin or paper towel on the lab bench.

The swatches were then read on the HunterLab Color Quest and calculate % soil removal (i.e. whiteness) from the difference between the initial (before washing) L value and the final L value (after washing). Percent Soil Removal=(L after−L initial)/(96−L initial)*100 is represented as L*.

TABLE 10

| (5 gpg) | | | | | | | | | |
|---|---|---|---|---|---|---|---|---|---|
| | EMPA 116 | | | EMPA 114 | | | EMPA 111 | | |
| | Before | After | % removal | Before | After | % removal | Before | After | % removal |
| 50 ppm Surfonic 24-3 | 42.99 | 54.4 | 27% | 77.28 | 78.94 | 2% | 50.12 | 74.92 | 49% |
| 50 ppm Surfonic 24-5 | 43.42 | 55.03 | 27% | 78.14 | 78.63 | 1% | 49.84 | 75.96 | 52% |
| 50 ppm Surfonic 24-7 | 43.02 | 54.58 | 27% | 78.4 | 78.38 | 0% | 49.4 | 72.16 | 46% |
| 50 ppm Surfonic 24-9 | 43.3 | 53.75 | 24% | 78.59 | 78.4 | 0% | 49.55 | 75.98 | 53% |
| 100 ppm Surfonic 24-3 | 42.82 | 53.27 | 24% | 78.11 | 78.24 | 0% | 49.66 | 73.51 | 48% |
| 100 ppm Surfonic 24-5 | 43.17 | 54.38 | 26% | 78.08 | 79 | 1% | 49.77 | 72.4 | 45% |
| 100 ppm Surfonic 24-7 | 42.94 | 56.01 | 30% | 78.22 | 77.82 | −1% | 49.72 | 72.28 | 45% |
| 100 ppm Surfonic 24-9 | 42.99 | 53.53 | 25% | 78.3 | 77.17 | −1% | 49.6 | 75.81 | 53% |
| 50 ppm Ethylhexylglycerine ether 1 mol EO | 43.27 | 54.59 | 26% | 77.98 | 78.07 | 0% | 49.81 | 73.99 | 49% |
| 50 ppm Ethylhexylglycerine ether 3 mol EO | 43.05 | 57.48 | 34% | 78.13 | 79.29 | 1% | 49.53 | 74.29 | 50% |
| 50 ppm Ethylhexylglycerine ether 5 mol EO | 43.07 | 56.07 | 30% | 78.1 | 79.4 | 2% | 49.49 | 73.19 | 48% |
| 50 ppm Ethylhexylglycerine ether 7 mol EO | 43.34 | 57.63 | 33% | 78.18 | 79.13 | 1% | 49.63 | 75.63 | 52% |
| 50 ppm | 42.82 | 56.96 | 33% | 78.32 | 79.73 | 2% | 49.36 | 72.87 | 48% |

TABLE 10-continued

| (5 gpg) | | | | | | | | |
|---|---|---|---|---|---|---|---|---|
| Ethylhexylglycerine ether 9 mol EO | | | | | | | | |
| 100 ppm Ethylhexylglycerine ether 1 mol EO | 42.96 | 54.36 | 27% | 78.32 | 77.63 | −1% | 49.2 | 74.9 | 52% |
| 100 ppm Ethylhexylglycerine ether 3 mol EO | 43.26 | 55.79 | 29% | 78.35 | 78.15 | 0% | 49.82 | 73.84 | 48% |
| 100 ppm Ethylhexylglycerine ether 5 mol EO | 42.94 | 55.03 | 28% | 78.34 | 78.92 | 1% | 49.53 | 71.7 | 45% |
| 100 ppm Ethylhexylglycerine ether 7 mol EO | 43.33 | 51.65 | 19% | 78.36 | 76.29 | −3% | 49.43 | 73.68 | 49% |
| 100 ppm Ethylhexylglycerine ether 9 mol EO | 43.11 | 53.72 | 25% | 78.43 | 78.38 | 0% | 49.35 | 75.96 | 54% |

| | EMPA 106 | | | EMPA 104 | | | EMPA 101 | | |
|---|---|---|---|---|---|---|---|---|---|
| | Before | After | % removal | Before | After | % removal | Before | After | % removal |
| 50 ppm Surfonic 24-3 | 59.26 | 40.02 | 52.63 | 40.02 | 52.63 | 32% | 45 | 60.82 | 35% |
| 50 ppm Surfonic 24-5 | 58.99 | 40.32 | 55.54 | 40.32 | 55.54 | 38% | 46.01 | 62.46 | 36% |
| 50 ppm Surfonic 24-7 | 59.45 | 39.99 | 51.08 | 39.99 | 51.08 | 28% | 44.82 | 61.8 | 38% |
| 50 ppm Surfonic 24-9 | 59.27 | 40.77 | 55.62 | 40.77 | 55.62 | 36% | 46.17 | 62.3 | 35% |
| 100 ppm Surfonic 24-3 | 58.92 | 40.46 | 50.72 | 40.46 | 50.72 | 25% | 45.77 | 58.78 | 28% |
| 100 ppm Surfonic 24-5 | 59.26 | 40.26 | 51.3 | 40.26 | 51.3 | 27% | 46.34 | 58.79 | 27% |
| 100 ppm Surfonic 24-7 | 59.12 | 40.61 | 49.7 | 40.61 | 49.7 | 22% | 46.6 | 59.33 | 27% |
| 100 ppm Surfonic 24-9 | 59.43 | 40.26 | 47.41 | 40.26 | 47.41 | 18% | 45.71 | 57.89 | 27% |
| 50 ppm Ethylhexylglycerine ether 1 mol EO | 59 | 40.14 | 50.77 | 40.14 | 50.77 | 26% | 45.57 | 57.89 | 27% |
| 50 ppm Ethylhexylglycerine ether 3 mol EO | 59.46 | 40.78 | 60.8 | 40.78 | 60.8 | 49% | 45.29 | 65.78 | 45% |
| 50 ppm Ethylhexylglycerine ether 5 mol EO | 59.45 | 40.28 | 59.51 | 40.28 | 59.51 | 48% | 45.47 | 63.71 | 40% |
| 50 ppm Ethylhexylglycerine ether 7 mol EO | 58.87 | 40.74 | 59.88 | 40.74 | 59.88 | 47% | 46.62 | 64.15 | 38% |
| 50 ppm Ethylhexylglycerine ether 9 mol EO | 58.9 | 40.08 | 55.18 | 40.08 | 55.18 | 38% | 46.08 | 60.75 | 32% |
| 100 ppm Ethylhexylglycerine ether 1 mol EO | 59.86 | 40.34 | 48.73 | 40.34 | 48.73 | 21% | 46.37 | 59.85 | 29% |
| 100 ppm Ethylhexylglycerine ether 3 mol EO | 59.82 | 40.22 | 50.39 | 40.22 | 50.39 | 25% | 45.53 | 58.58 | 29% |
| 100 ppm Ethylhexylglycerine ether 5 mol EO | 59.2 | 40.2 | 49.62 | 40.2 | 49.62 | 23% | 45.58 | 58.99 | 29% |
| 100 ppm Ethylhexylglycerine ether 7 mol EO | 59.36 | 39.86 | 46.8 | 39.86 | 46.8 | 17% | 45.12 | 56.47 | 25% |
| 100 ppm Ethylhexylglycerine ether 9 mol EO | 59.74 | 40.52 | 50.14 | 40.52 | 50.14 | 24% | 45.49 | 58.62 | 29% |

TABLE 11

(17 gpg)

| | EMPA 116 | | | EMPA 114 | | | EMPA 111 | | |
|---|---|---|---|---|---|---|---|---|---|
| | Before | After | % removal | Before | After | % removal | Before | After | % removal |
| 50 ppm Surfonic 24-3 | 43.55 | 49.87 | 15% | 77.95 | 76.72 | −2% | 49.49 | 61.15 | 24% |
| 50 ppm Surfonic 24-5 | 43.91 | 45.84 | 4% | 78.07 | 79.92 | 2% | 49.21 | 61.41 | 25% |
| 50 ppm Surfonic 24-7 | 43.47 | 52.05 | 20% | 78.08 | 78.21 | 0% | 48.95 | 63.27 | 29% |
| 50 ppm Surfonic 24-9 | 43.54 | 52.32 | 20% | 78.06 | 79.42 | 2% | 49.36 | 63.33 | 28% |
| 100 ppm Surfonic 24-3 | 43.34 | 48.6 | 12% | 78.04 | 77.32 | −1% | 49.15 | 61.02 | 24% |
| 100 ppm Surfonic 24-5 | 43.77 | 54.72 | 25% | 77.85 | 78.5 | 1% | 49.09 | 69.23 | 41% |
| 100 ppm Surfonic 24-7 | 43.26 | 53.19 | 23% | 78.01 | 78.69 | 1% | 49.09 | 65.17 | 33% |
| 100 ppm Surfonic 24-9 | 43.54 | 53.97 | 24% | 77.96 | 79.01 | 1% | 49.09 | 65.32 | 33% |
| 50 ppm Ethylhexylglycerine ether 1 mol EO | 43.26 | 50.61 | 17% | 77.98 | 77.77 | 0% | 49.27 | 65.09 | 32% |
| 50 ppm Ethylhexylglycerine ether 3 mol EO | 43.24 | 49.53 | 15% | 77.78 | 76.53 | −2% | 49.41 | 63.73 | 29% |
| 50 ppm Ethylhexylglycerine ether 5 mol EO | 43.37 | 50.77 | 17% | 77.92 | 78.3 | 0% | 49.12 | 64.1 | 30% |
| 50 ppm Ethylhexylglycerine ether 7 mol EO | 43.25 | 50.08 | 16% | 77.85 | 77.8 | 0% | 49.18 | 64.86 | 32% |
| 50 ppm Ethylhexylglycerine ether 9 mol EO | 43.6 | 52.78 | 21% | 77.82 | 78.88 | 1% | 49.05 | 66.2 | 35% |
| 100 ppm Ethylhexylglycerine ether 1 mol EO | 43.36 | 50.78 | 17% | 78.09 | 77.57 | −1% | 49.25 | 64.18 | 30% |
| 100 ppm Ethylhexylglycerine ether 3 mol EO | 43.55 | 50.69 | 16% | 78.12 | 77.33 | −1% | 49.18 | 62.53 | 27% |
| 100 ppm Ethylhexylglycerine ether 5 mol EO | 43.31 | 52.09 | 20% | 78.12 | 78 | 0% | 49.09 | 69.37 | 41% |
| 100 ppm Ethylhexylglycerine ether 7 mol EO | 43.59 | 50.8 | 17% | 78.12 | 78.36 | 0% | 49.05 | 66.21 | 35% |
| 100 ppm Ethylhexylglycerine ether 9 mol EO | 43.27 | 51.9 | 20% | 78.05 | 78.66 | 1% | 49.17 | 65.12 | 32% |

| | EMPA 106 | | | EMPA 104 | | | EMPA 101 | | |
|---|---|---|---|---|---|---|---|---|---|
| | Before | After | % removal | Before | After | % removal | Before | After | % removal |
| 50 ppm Surfonic 24-3 | 57.68 | 65.38 | 13% | 40.14 | 45.22 | 13% | 46.27 | 53.93 | 17% |
| 50 ppm Surfonic 24-5 | 58.14 | 64.25 | 11% | 40.4 | 50.65 | 25% | 45.96 | 56.92 | 24% |
| 50 ppm Surfonic 24-7 | 57.9 | 67.97 | 17% | 39.8 | 49.44 | 24% | 45.81 | 56.94 | 24% |
| 50 ppm Surfonic 24-9 | 58.44 | 64.47 | 10% | 40.27 | 48.77 | 21% | 46.05 | 57.35 | 25% |
| 100 ppm Surfonic 24-3 | 57.92 | 66.73 | 15% | 40.14 | 47.27 | 18% | 45.71 | 54.85 | 20% |
| 100 ppm Surfonic 24-5 | 58.59 | 65.5 | 12% | 40.18 | 49.92 | 24% | 47 | 58.79 | 25% |
| 100 ppm Surfonic 24-7 | 57.62 | 65.99 | 15% | 40.05 | 51.21 | 28% | 46.33 | 58.38 | 26% |
| 100 ppm Surfonic 24-9 | 58.3 | 67.65 | 16% | 40.11 | 50.72 | 26% | 46.17 | 60 | 30% |
| 50 ppm Ethylhexylglycerine ether 1 mol EO | 59.15 | 62.95 | 6% | 40 | 45.77 | 14% | 47.27 | 56.26 | 19% |
| 50 ppm | 57.78 | 65.61 | 14% | 40.07 | 46.24 | 15% | 46.2 | 54.13 | 17% |

TABLE 11-continued

| | (17 gpg) | | | | | | | | |
|---|---|---|---|---|---|---|---|---|---|
| Ethylhexylglycerine ether 3 mol EO 50 ppm | 58.45 | 65.89 | 13% | 40.23 | 46.34 | 15% | 47.26 | 56.23 | 19% |
| Ethylhexylglycerine ether 5 mol EO 50 ppm | 57.92 | 64.52 | 11% | 39.81 | 45.88 | 15% | 46.9 | 56.14 | 20% |
| Ethylhexylglycerine ether 7 mol EO 50 ppm | 59.09 | 64.47 | 9% | 40.09 | 47.68 | 19% | 47.1 | 57.2 | 21% |
| Ethylhexylglycerine ether 9 mol EO 100 ppm | 59.01 | 63.32 | 7% | 40.11 | 46.26 | 15% | 46.87 | 55.23 | 18% |
| Ethylhexylglycerine ether 1 mol EO 100 ppm | 58.66 | 63.65 | 9% | 40.09 | 45.42 | 13% | 47 | 55.7 | 19% |
| Ethylhexylglycerine ether 3 mol EO 100 ppm | 58.75 | 65.46 | 11% | 39.86 | 47.24 | 19% | 46.24 | 55.85 | 21% |
| Ethylhexylglycerine ether 5 mol EO 100 ppm | 59.11 | 64.71 | 9% | 40.09 | 46.8 | 17% | 46.26 | 55.46 | 20% |
| Ethylhexylglycerine ether 7 mol EO 100 ppm | 59.4 | 65.4 | 10% | 39.82 | 46.04 | 16% | 47.09 | 56.73 | 20% |
| Ethylhexylglycerine ether 9 mol EO | | | | | | | | | |

As shown in Tables 10-11 the solfactant laundry detergent compositions provided at least substantially similar cleaning efficacy as the conventional Surfonic®-based compositions. Beneficially, in addition to the cleaning efficacy, the solfactants further enable increased concentrations of the laundry formulations due to the low viscosity that results from use of the solfactants.

Example 9

The glycerin ether ethoxylate solfactants were also formulated into sanitizing compositions employing quaternary ammonium cations, such as shown in the concentrate formula of Table 12.

TABLE 12

| Component | Solfactant Formula wt-% |
|---|---|
| Water | 41.75 |
| Bardac 205M (Quat sanitizer) | 10.25 |
| 2 ethylhexyl glycerine ether | 48 |
| (3 moles EO) | |
| | 100 |

As the solfactants are shown to provide beneficial cleaning on both red and black soils (see Example 4), the further formulation into sanitizing compositions with quaternary ammonium cations provides the additional benefit of allowing simultaneous cleaning and sanitizing in a single composition. Without being limited to a particular theory and/or mechanism of action of the present invention, the solfactant-based quat composition does not form micelles with the quaternary ammonium cations, as occurs with ethoxylated alcohols (e.g. Tomadol) and various other surfactant classes. In addition, the various formulations according to the invention, including for example CIP cleaning and/or sanitizing compositions, illustrate further benefits of the solfactants according to the invention; namely the highly concentrated use of the glycerin ether ethoxylates without forming gels (in some embodiments) and/or becoming too viscous. Instead, the compositions provide flowable and/or pourable compositions which can be further concentrated.

Example 10

The water solubility of the glycerin ether ethoxylate solfactants were compared to conventional alcohol ethoxylate surfactants having equivalent degrees of ethoxylation (e.g. moles ethoxylation), as shown in Table 13.

TABLE 13

| Moles of ethoxylation | Surfactant/Solfactant | % Soluble |
|---|---|---|
| Zero | 2 Ethylhexanol | Insoluble |
| Zero | 2 Ethylhexyl glycerin ether | Insoluble |
| 1 mole | 2 Ethylhexyl 1 mole | Insoluble |
| 1 mole | 2 Ethylhexyl glycerine ether 1 mole | Insoluble |
| 3 moles | 2 Ethylhexyl 3 mole | Insoluble |
| 3 moles | 2 Ethylhexyl glycerine ether 3 mole | 100% |
| 5 moles | 2 Ethylhexyl 5 mole | Partially soluble |
| 5 moles | 2 Ethylhexyl glycerine ether 5 mole | 100% |

Example 11

Differential Scanning calorimetry (DSC) was run on the various 2-Ethyl Hexanol Glycerin Ether Ethoxylate solfactants set forth in Table 1. The DSC evaluated additional properties of the exemplary set of novel solfactants, namely the freezing point of the molecules.

Figure 4A:
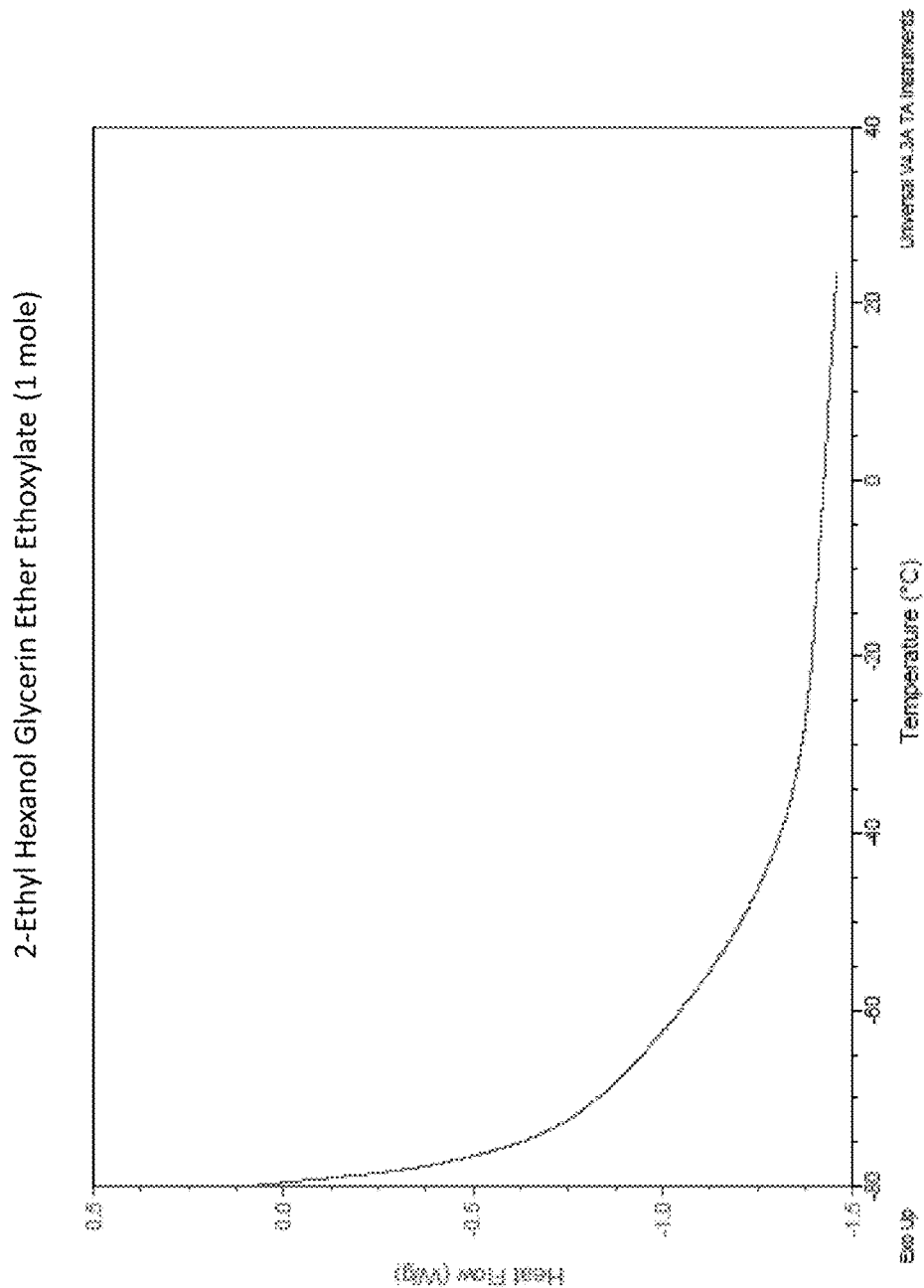
FIGS. 4A-4E show DSC measurements of various glycerin ether ethoxylate solfactants according to embodiments of the invention, demonstrating the low temperature stability.
Figure 4B:
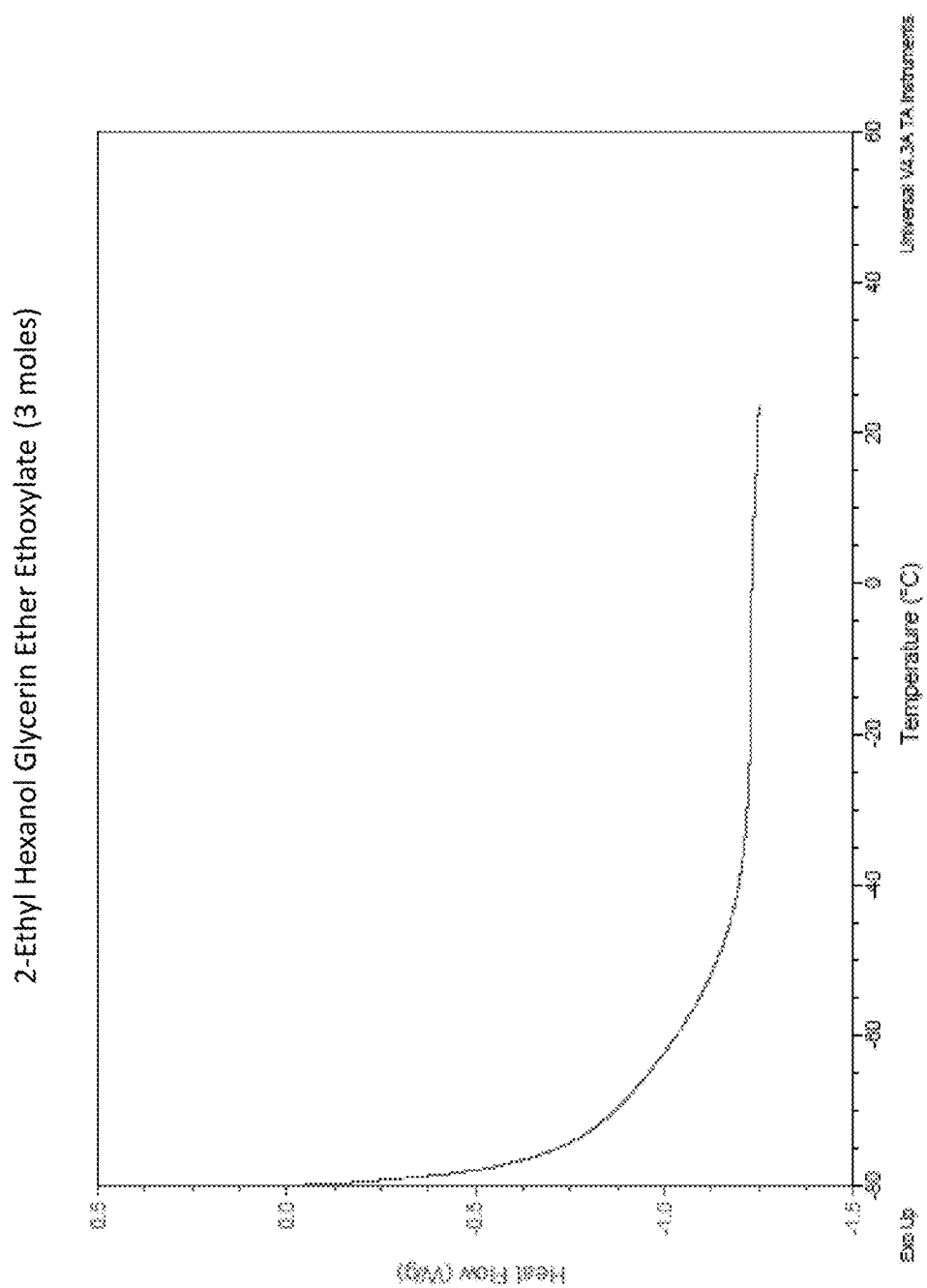
Figure 4C:
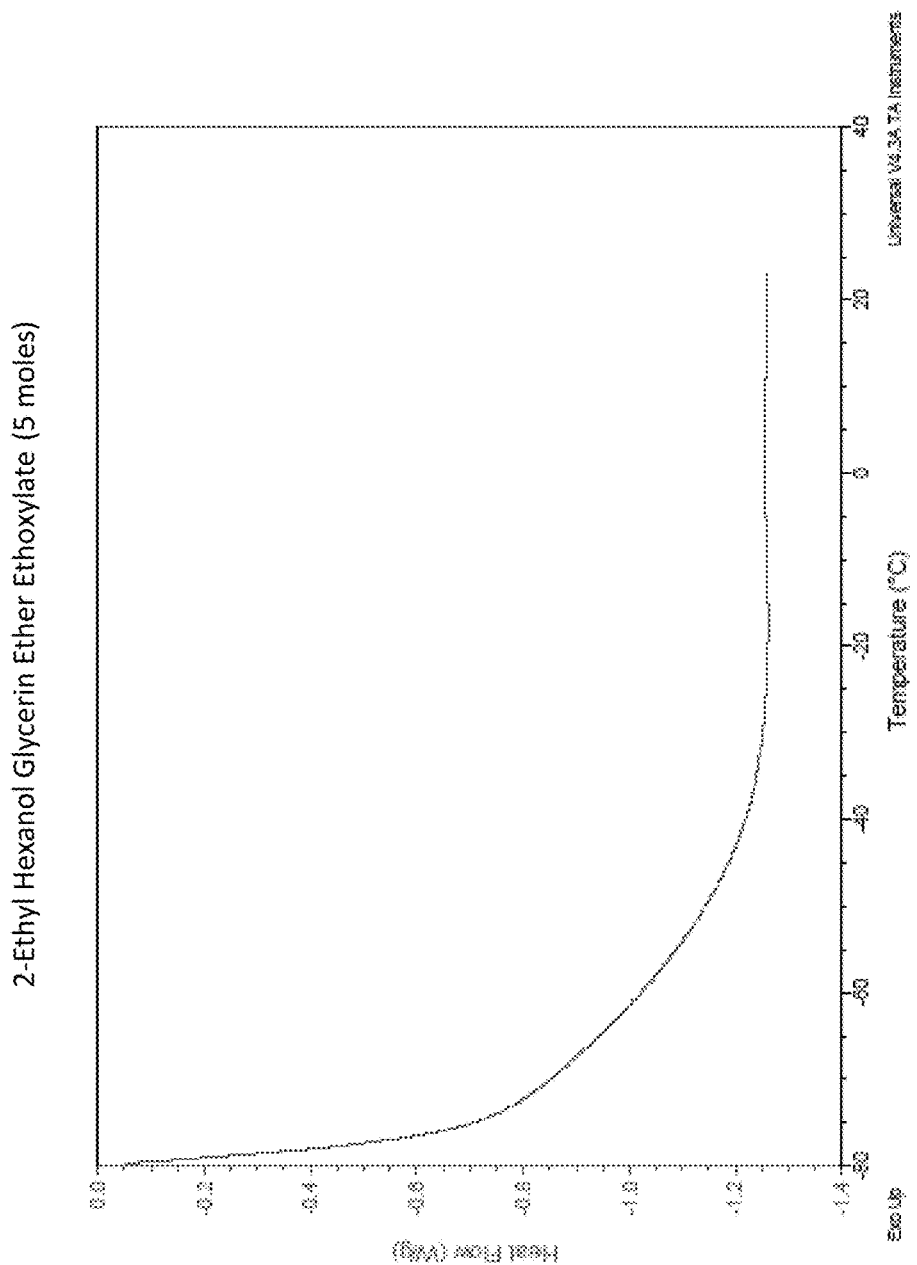
Figure 4D:
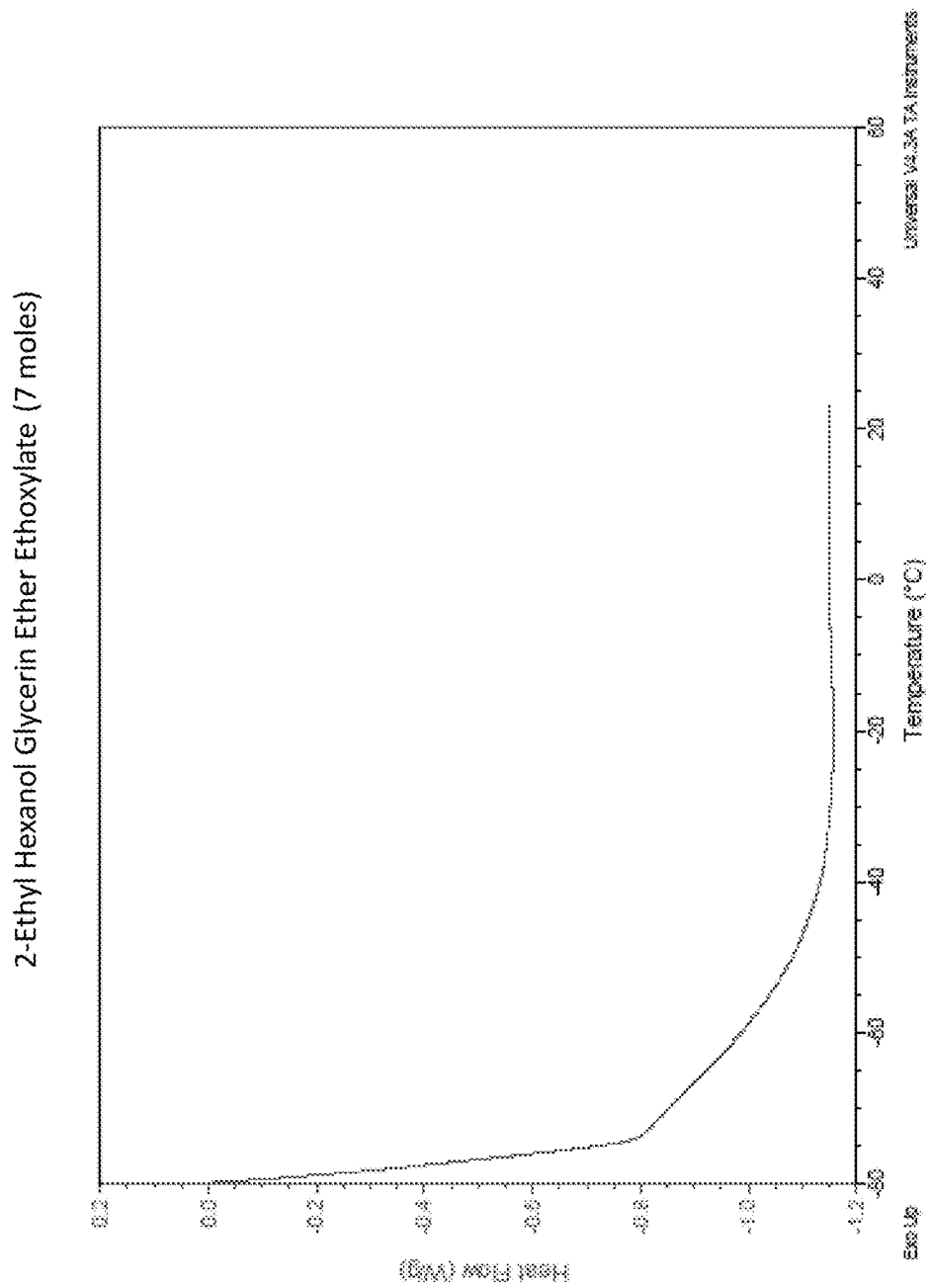
Figure 4E:
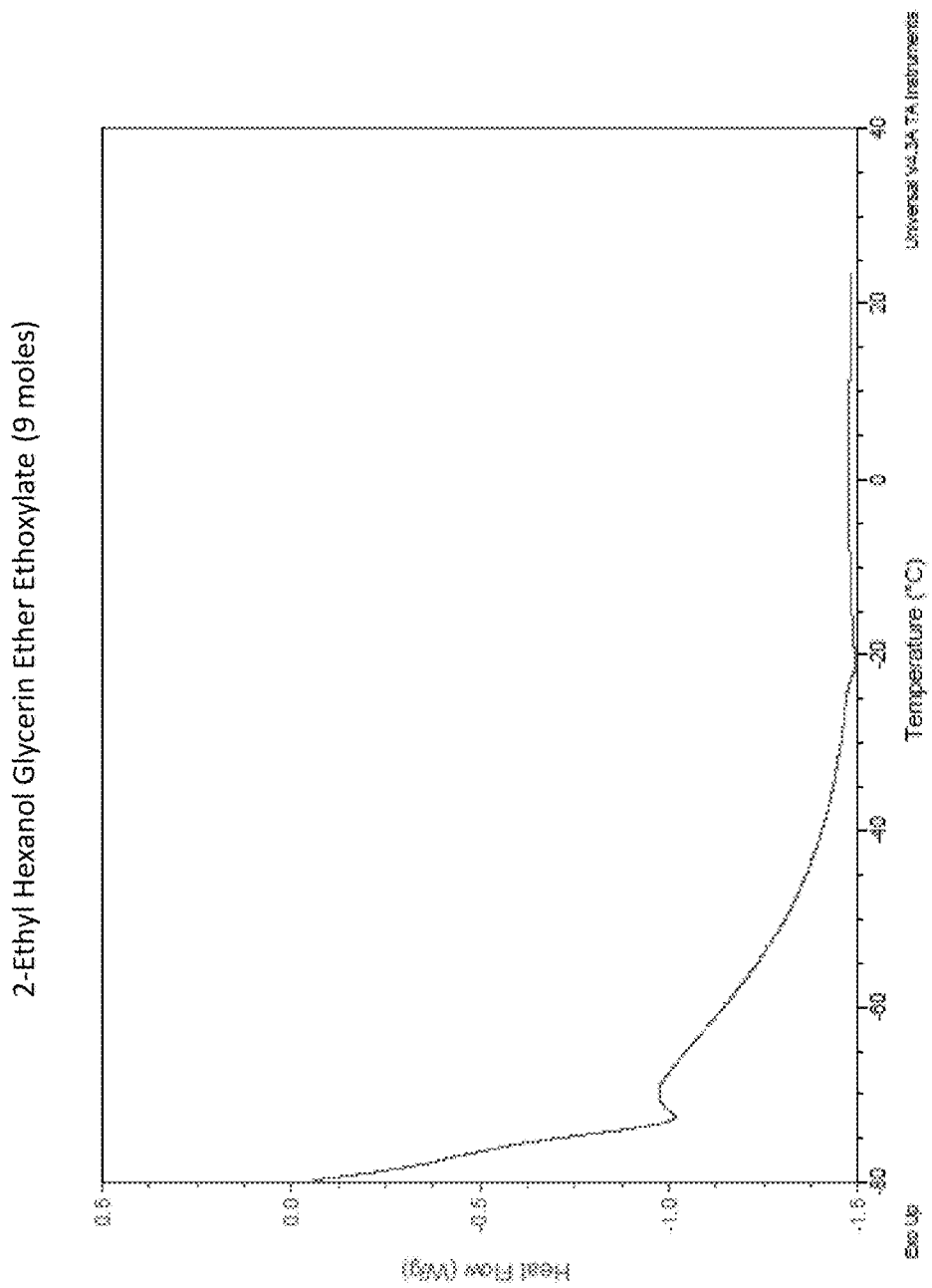

The DSC utilized can be measured down to minus 80° C. for determining a freeze or melt points of a liquid. As shown in FIGS. 4A-4E, all evaluated glycerin ether ethoxylates remained liquids without freezing down to the measured minus 80° C., including 2-Ethyl Hexanol Glycerin Ether Ethoxylate (1 mole) (FIG. 4A), 2-Ethyl Hexanol Glycerin Ether Ethoxylate (3 moles) (FIG. 4B), 2-Ethyl Hexanol Glycerin Ether Ethoxylate (5 moles) (FIG. 4C), 2-Ethyl Hexanol Glycerin Ether Ethoxylate (7 moles) (FIG. 4D), and 2-Ethyl Hexanol Glycerin Ether Ethoxylate (9 moles) (FIG. 4E). This is distinct form conventional alcohol ethoxylates (having equivalent degrees of ethoxylation) which have very high melt points. For example, many conventional alcohol ethoxylate surfactants have melt points at room temperature or higher, resulting in the compositions being solids at room temperature. In addition, as one skilled in the art ascertains, the more ethyl oxide you add to a standard alcohol ethoxylate, the higher the melt point. This is distinct from the solfactants according to the invention, including the 2-Ethyl Hexanol Glycerin Ether Ethoxylate solfactants set forth in Table 1. For example, Tomadol 24-9 is a solid at room temperature, whereas the equivalent 2EHGE 9 mole is a liquid at room temperature.

This data demonstrates a further beneficial characteristic of the solfactants according to the invention, namely their stability in low temperature formulations. Unlike conventional ethoxylated alcohol surfactants, the glycerin ether ethoxylate solfactants according to the invention may be included in a broad range of formulations and applications of use under low temperatures.

Example 12

A non-food contact sanitizing efficacy test was conducted to compare sanitizing efficacy of two quaternary ammonium compound formulations, at varying concentrations, comparing combination with an alcohol ethoxylate (commercially-available as Tomadol 24-7) versus the glycerin ether ethoxylate (2 ethylhexyl glycerin ether 3 mole) at constant concentrations (0.38 wt-% of the composition) against *Staphylococcus aureus* ATCC 6538 at ambient temperatures. The compositions each employed a commercially-available quaternary ammonium compound Bardac 205M. A 30 second and 5 minute exposure time were utilized to test the sanitizing efficacy of compositions. Table 14 shows the dried coupon inoculum controls, wherein the count of *Staphylococcus aureus* suspension used to inoculate coupons was $6.5 \times 10^8$ CFU/mL.

TABLE 14

| Replicate | CFU/plate | Dilution | Avg CFU/mL | Total Organism surviving per square (×25) | Log10 | Geometric Mean |
|---|---|---|---|---|---|---|
| 1 | 48, 41 | $10^{-4}$ | $4.5 \times 10^5$ | $1.1 \times 10^7$ | 7.04 | |
| 2 | 39, 29 | $10^{-4}$ | $3.4 \times 10^5$ | $8.5 \times 10^6$ | 6.92 | |
| 3 | 40, 46 | $10^{-4}$ | $4.3 \times 10^5$ | $1.1 \times 10^7$ | 7.04 | |
| 4 | 378, 297 | $10^{-3}$ | $2.7 \times 10^5$ | $6.8 \times 10^6$ | 6.83 | $9.1 \times 10^6$ |
|   | 19, 23 | $10^{-4}$ | | | | |

The test systems used a 1×1 inch stainless steel squares were employed. Ambient testing temperature (18-22° C.); exposure time of 30 seconds and 5 minutes; neutralizer media 20 mL Dey-Engley (DE) broth were employed. A neutralizer screen was performed as part of the testing, verified that the neutralizer adequately neutralized the product and was not detrimental to the tested organisms. Plating Medium utilized was Tryptone Glucose Extract (TGE) agar and organisms were incubated at 35° C. for 48 hours.

Table 15 shows the results for the 5 minute exposure time of the *Staphylococcus aureus* to the Control and Test formulations (GEE containing as a replacement for alcohol ethoxylates) having variations in solvent concentration.

TABLE 15

| Test Substance | Rep | Avg CFU/mL | Total Organisms surviving per coupon (×25) | Log10 | Geometric Mean | Percent Reduction |
|---|---|---|---|---|---|---|
| 400 ppm | 1 | 4.5 | $1.1 \times 10^2$ | 2.05 | $<3.6 \times 10^1$ | >99.999 |
| Quat 205M | 2 | <1 | <25 | <1.39 | | |
| GEE 3 mole | 3 | 1.5 | $3.8 \times 10^1$ | 1.57 | | |
|  | 4 | <1 | <25 | <1.39 | | |
|  | 5 | <1 | <25 | <1.39 | | |
| 400 ppm | 1 | <1 | <25 | <1.39 | $<3.2 \times 10^1$ | >99.999 |
| Quat 205M | 2 | <1 | <25 | <1.39 | | |
| Tomadol | 3 | 3.5 | $8.8 \times 10^1$ | 1.94 | | |
| 24-7 | 4 | <1 | <25 | <1.39 | | |
|  | 5 | <1 | <25 | <1.39 | | |
| 800 ppm | 1 | <1 | <25 | <1.39 | $<2.4 \times 10^1$ | >99.999 |
| Quat 205M | 2 | <1 | <25 | <1.39 | | |
| GEE 3 mole | 3 | <1 | <25 | <1.39 | | |
|  | 4 | <1 | <25 | <1.39 | | |
|  | 5 | <1 | <25 | <1.39 | | |
| 800 ppm | 1 | <1 | <25 | <1.39 | $<2.4 \times 10^1$ | >99.999 |
| Quat 205M | 2 | <1 | <25 | <1.39 | | |
| Tomadol | 3 | <1 | <25 | <1.39 | | |
| 24-7 | 4 | <1 | <25 | <1.39 | | |
|  | 5 | <1 | <25 | <1.39 | | |

Table 15 demonstrates the average log survivors of *Staphylococcus aureus* observed after a 5 minute exposure to the Control and Test formulations. Both compositions provided sanitizing efficacy at the extended exposure time of 5 minutes. Therefore, a reduced contact time was evaluated to provide persons employing the compositions with a reduced time of exposure required for sanitizing efficacy without having to increase the concentration of quaternary ammonium compound employed in the sanitizing composition.

The subsequent test system employed was the same with the exception of the decreased contact time of 30 seconds. Table 16 shows the dried coupon inoculum controls, wherein the count of *Staphylococcus aureus* suspension used to inoculate coupons was $9.6 \times 10^8$ CFU/mL.

TABLE 16

| Replicate | CFU/plate | Dilution | Avg CFU/mL | Total Organism surviving per square (×25) | Log10 | Geometric Mean |
|---|---|---|---|---|---|---|
| 1 | 17, 19 | $10^{-4}$ | $2.6 \times 10^5$ | $6.6 \times 10^6$ | 6.81 | |
|   | 371, 317 | $10^{-3}$ | | | | |
| 2 | 24, 31 | $10^{-4}$ | $2.8 \times 10^5$ | $6.9 \times 10^6$ | 6.83 | |
| 3 | 41, 39 | $10^{-4}$ | $4.0 \times 10^5$ | $1.0 \times 10^7$ | 7.00 | |
| 4 | 30, 39 | $10^{-4}$ | $3.5 \times 10^5$ | $8.6 \times 10^6$ | 6.93 | $7.8 \times 10^6$ |

Table 17 shows the results for the shortened 30 second exposure time of the *Staphylococcus aureus* to the Control and Test formulations (GEE containing as a replacement for alcohol ethoxylates) having variations in solvent concentration.

TABLE 17

| Test Substance | Rep | Avg CFU/mL | Total organisms surviving per coupon (×25) | Log10 | Geometric Mean | Percent Reduction |
|---|---|---|---|---|---|---|
| 400 ppm Quat 205M GEE 3 mole | 1 | 2 | $5 \times 10^1$ | 1.69 | $<5.2 \times 10^1$ | >99.999 |
| | 2 | <1 | <25 | <1.39 | | |
| | 3 | <1 | <25 | <1.39 | | |
| | 4 | $1.4 \times 10^1$ | $3.5 \times 10^2$ | 2.54 | | |
| | 5 | 1.5 | $3.8 \times 10^1$ | 1.57 | | |
| 400 ppm Quat 205M Tomadol 24-7 | 1 | $2.4 \times 10^3$ | $6.0 \times 10^4$ | 4.77 | $2.2 \times 10^4$ | 99.7 |
| | 2 | $7.9 \times 10^1$ | $2.0 \times 10^3$ | 3.29 | | |
| | 3 | $1.7 \times 10^3$ | $4.1 \times 10^4$ | 4.61 | | |
| | 4 | $4.6 \times 10^1$ | $1.1 \times 10^3$ | 3.05 | | |
| | 5 | $4.3 \times 10^4$ | $1.1 \times 10^6$ | 6.03 | | |
| 800 ppm Quat 205M GEE 3 mole | 1 | $2.1 \times 10^1$ | $5.3 \times 10^2$ | 2.72 | $<2.8 \times 10^2$ | >99.996 |
| | 2 | <2 | $<5.0 \times 10^1$ | <1.69 | | |
| | 3 | 1.5 | $3.8 \times 10^1$ | 1.57 | | |
| | 4 | $4.6 \times 10^1$ | $1.1 \times 10^3$ | 3.05 | | |
| | 5 | $6.4 \times 10^1$ | $1.6 \times 10^3$ | 3.20 | | |
| 800 ppm Quat 205M Tomadol 24-7 | 1 | <1.5 | $3.8 \times 10^1$ | <1.57 | $<1.1 \times 10^4$ | >99.8 |
| | 2 | $2.0 \times 10^2$ | $5.0 \times 10^3$ | 3.70 | | |
| | 3 | $6.0 \times 10^3$ | $1.5 \times 10^5$ | 5.17 | | |
| | 4 | $1.7 \times 10^3$ | $4.3 \times 10^4$ | 4.62 | | |
| | 5 | $6.0 \times 10^3$ | $1.5 \times 10^5$ | 5.17 | | |

Table 17 demonstrates the shorter exposure time results in both concentrations of the Test formulations (containing GEE in place of the alcohol ethoxylate) providing sanitizing efficacy. Neither concentration of the quaternary ammonium compound/alcohol ethoxylate provided sanitizing efficacy (requiring a greater than 3 log reduction) at 30 second exposure time (e.g. short time exposure are desired by users for application and prompt cleaning thereafter without requiring substantial resting time to allow additional sanitizing performance). Without being bound to a particular mechanism of action for the present invention, it is hypothesized that the alcohol ethoxylates form micelles with the quaternary ammonium compounds when combined and therefore result in diminished performance requiring either increased concentrations of use and/or increased exposure time to provide equivalent sanitizing efficacy to the quaternary ammonium compounds and glycerin ether ethoxylates (solfactants according to the invention).

As demonstrated according to embodiments of the invention, the sanitizing compositions containing the solfactants provide beneficial sanitizing efficacy at minimized concentrations and without requiring extended contact time to provide necessary kill for sanitization. This is beneficial as persons employing the compositions require sanitizing efficacy at a minimal exposure, such as enabling a person employing the sanitizing composition to spray a composition onto a surface and promptly wipe the surface to remove soils and sanitize. In an aspect, the sanitizing compositions provide sanitizing efficacy upon contact from at least a few seconds to a few minutes, or from at least 30 seconds.

Example 13

Additional non-food contact sanitizing efficacy tests were conducted to compare sanitizing efficacy of quaternary ammonium compound formulations, at varying concentrations, in combination with a glycerin ether ethoxylate (2 ethylhexyl glycerin ether 3 mole, maintained in each composition at 0.38 wt-%) against Staphylococcus aureus ATCC 6538 at ambient temperature. The compositions each employed the commercially-available quaternary ammonium compound Bardac 205M at varying concentrations from 0 ppm, 100 ppm, 200 ppm, 300 ppm, and 400 ppm. The same methodology and conditions as Example 12 were employed.

Table 18 shows the dried coupon inoculum controls, wherein the count of Staphylococcus aureus suspension used to inoculate coupons was $1 \times 10^9$ CFU/mL.

TABLE 18

| Replicate | CFU/plate | Dilution | Avg CFU/mL | Total Organism surviving per square (×25) | Log10 | Geometric Mean |
|---|---|---|---|---|---|---|
| 1 | 48, 33 | $10^{-4}$ | $4.1 \times 10^5$ | $1.0 \times 10^7$ | 7.00 | $1.2 \times 10^7$ |
| 2 | 74, 54 | $10^{-4}$ | $6.4 \times 10^5$ | $1.6 \times 10^7$ | 7.2 | |
| 3 | 48, 42 | $10^{-4}$ | $4.5 \times 10^5$ | $1.1 \times 10^7$ | 7.05 | |
| 4 | 48, 43 | $10^{-4}$ | $4.6 \times 10^5$ | $1.1 \times 10^7$ | 7.05 | |

Table 19 shows the results for the 30 second exposure time of the Staphylococcus aureus to the Test formulations (GEE containing as a replacement for alcohol ethoxylates in combination with various quat concentrations).

TABLE 19

| Test Substance | Rep | Avg CFU/mL | Total Organisms surviving per coupon (×25) | Log10 | Geometric mean | Percent Reduction |
|---|---|---|---|---|---|---|
| 400 ppm Quat 205M GEE 3 mole | 1 | <1 | <25 | <1.39 | $<2.5 \times 10^1$ | >99.999 |
| | 2 | 1 | 25 | 1.39 | | |
| | 3 | <1 | <25 | <1.39 | | |
| | 4 | 1 | 25 | 1.39 | | |
| | 5 | <1 | <25 | <1.39 | | |
| 300 ppm Quat 205M GEE 3 mole | 1 | <1 | <25 | <1.39 | $<1.1 \times 10^2$ | >99.999 |
| | 2 | <1 | <25 | <1.39 | | |
| | 3 | 5 | $1.1 \times 10^2$ | 2.05 | | |
| | 4 | $3.2 \times 10^2$ | $8.0 \times 10^3$ | 3.90 | | |
| | 5 | <1 | <25 | <1.39 | | |
| 200 ppm Quat 205M GEE | 1 | $1.0 \times 10^2$ | $2.5 \times 10^3$ | 3.4 | $7.2 \times 10^2$ | 99.994 |
| | 2 | $4.8 \times 10^1$ | $1.2 \times 10^3$ | 3.07 | | |
| | 3 | 1 | 25 | 1.39 | | |
| | 4 | 9 | $2.3 \times 10^2$ | 2.35 | | |

TABLE 19-continued

| Test Sub-stance | Rep | Avg CFU/mL | Total Organisms surviving per coupon (x25) | Log10 | Geo-metric mean | Percent Reduction |
|---|---|---|---|---|---|---|
| 3 mole 100 ppm Quat | 5 | $4.8 \times 10^2$ | $1.2 \times 10^4$ | 4.08 | $2.6 \times 10^4$ | 99.78 |
| 205M | 1 | $9.2 \times 10^3$ | $2.3 \times 10^5$ | 5.36 | | |
| GEE | 2 | $2.2 \times 10^2$ | $5.6 \times 10^3$ | 3.74 | | |
| 3 mole | 3 | $8.6 \times 10^3$ | $2.2 \times 10^5$ | 5.33 | | |
| 0 ppm Quat | 4 | $2.3 \times 10^2$ | $5.8 \times 10^3$ | 3.76 | | |
| | 5 | $2.9 \times 10^2$ | $7.3 \times 10^3$ | 3.86 | | |
| | 1 | $5.5 \times 10^5$ | $1.4 \times 10^7$ | 7.13 | $1.1 \times 10^7$ | 8.3 |
| 205M | 2 | $5.1 \times 10^5$ | $1.3 \times 10^7$ | 7.10 | | |
| GEE | 3 | $3.2 \times 10^5$ | $7.9 \times 10^6$ | 6.89 | | |
| 3 mole | 4 | $5.1 \times 10^5$ | $1.3 \times 10^7$ | 7.10 | | |
| | 5 | $3.2 \times 10^5$ | $8.0 \times 10^6$ | 6.90 | | |

Table 19 demonstrates that with the 30 second exposure the 200 ppm, 300 ppm and 400 ppm Quat formulations passed the non-food contact sanitizing requirements of achieving at least a 3 log reduction in the *Staphylococcus aureus*. The 100 ppm Quat formulation did not achieve the sanitizing efficacy with the 30 second exposure time at ambient temperatures, although a reduction was achieved. The 0 ppm Quat formulation did not demonstrate any significant reduction.

Example 14

The disinfectant efficacy of a commercial quaternary ammonium sanitizing composition (Control) was compared to the sanitizing efficacy of a composition including a glycerin ether ethoxylate (2 ethylhexyl glycerin ether 3 mole) and a quaternary ammonium compound. The commercial sanitizing composition contains a quaternary ammonium compound in a ready-to-use solution with Tomadol (alcohol ethoxylate), EDTA and sodium metasilicate. The sanitizing composition according to the invention provided a disinfectant formulation at equal wt-% of the quaternary ammonium compound as in the commercially-available Control composition. The efficacy was evaluated against *Staphylococcus aureus* ATCC 6538 using 400 ppm hard water at a concentration of 1:256 with 5% soil at 5 minute exposure time at 20° C.

Table 20 shows the use dilution efficacy of the compositions, wherein a product passes the use dilution test if at least 59 out of 60 tubes tested are negative for *Staphylococcus aureus*.

TABLE 20

| Test Substance | Exposure Time (minutes) | # negative tubes/# tubes tested | Pass/Fail |
|---|---|---|---|
| Control Composition (Quat/Alcohol ethoxylate) | 5 | 26/30 | Fail |
| Sanitizing Composition Containing GEE 3 mole | 5 | 30/30 | Pass |

As shown in Table 20 the Control formulation containing the alcohol ethoxylate (instead of the GEE according to an embodiment of the invention) fails to provide a passing use dilution for disinfectant activity. In comparison, the formulation containing the GEE with quaternary ammonium compound when prepared in 400 ppm hard water at concentration of 1:256 achieves disinfectant efficacy with a 30 carrier screen against *Staphylococcus aureus* with a 5% soil load after a 5 minute exposure at 20° C.

The above specification provides a description of the manufacture and use of the disclosed compositions and methods. The inventions being thus described, it will be obvious that the same may be varied in many ways. Such variations are not to be regarded as a departure from the spirit and scope of the inventions and all such modifications are intended to be included within the scope of the following claims.

What is claimed is:

1. A sanitizing composition consisting of:
   a quaternary ammonium containing compound or a salt thereof; water;
   a solfactant compound according to the following formula:

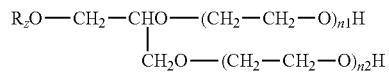

$$R_zO\text{---}CH_2\text{---}CHO\text{---}(CH_2\text{---}CH_2\text{---}O)_{n1}H$$
$$CH_2O\text{---}(CH_2\text{---}CH_2\text{---}O)_{n2}H$$

wherein $R_z$ is $CH_3$, $CH_3CH_2$, or a linear or branched alkyl group having 1 to 30 carbon atoms;
   wherein $n_1$ is 1 to 25;
   wherein $n_2$ is 1 to 25; and
   one or more agents selected from the group consisting of solvent, diluent, dye, and pigment, wherein the solfactant compound is water soluble and the composition is a sanitizing composition.

2. The composition of claim 1, wherein $R_z$ is a branched or linear alkyl group having 1 to 25 carbon atoms.

3. The composition of claim 1, wherein $R_z$ is a branched or linear alkyl group having 1 to 25 carbon atoms and does not form a gel when combined with any concentration of water.

4. The composition of claim 1, wherein $n_1$ is 1 to 20, wherein $n_2$ is 1 to 20, wherein the degree of ethoxylation may vary between the two ethoxylated tails of the solfactant composition, and wherein the solfactant has a molecular weight from about 200 to about 10,000 Da and is a substitute for alcohol ethoxylates.

5. The composition of claim 1, wherein the quaternary ammonium containing compound has one of the following formulas:

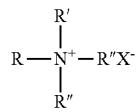

$$R\text{---}\underset{\underset{R''}{|}}{\overset{\overset{R'}{|}}{N^+}}\text{---}R'''X^-$$

wherein R, R', R" and R''' are each independently alkyl groups, aliphatic groups, aromatic groups, alkoxy groups, polyoxyalkylene groups, alkylamido groups, hydroxyalkyl groups, aryl groups, and/or H+ ions, each having from 1 to 22 carbon atoms, wherein at least one of R, R', R" and/or R''' has at least 8 carbon atoms, and wherein $X^{(-)}$ is an anion;

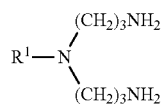

$$R^1\text{---}N\underset{\diagdown (CH_2)_3NH_2}{\diagup (CH_2)_3NH_2}$$

wherein $R^1$ is a $C_1$-$C_{20}$ alkyl group.

6. The composition of claim 1, wherein the quaternary ammonium containing compound is an alkylated quaternary ammonium compound, ring or cyclic quaternary ammonium compound, aromatic quaternary ammonium compound, diquaternary ammonium compound, alkoxylated quaternary ammonium compound, amidoamine quaternary ammonium compound, ester quaternary ammonium compound, alkanolamine, triamine and/or mixtures thereof.

7. A sanitizing composition consisting of:
a quaternary ammonium containing compound or a salt thereof; water; and
a solfactant compound according to the following formula:

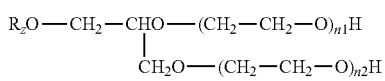

wherein $R_z$ is a branched or linear alkyl group having 1 to 25 carbon atoms;
wherein $n_1$ is 1 to 20;
wherein $n_2$ is 1 to 20;
the molecular weight of the surfactant is from about 200 to about 10,000 Da;
the compound is water soluble, and the composition is a sanitizing composition.

8. The composition of claim 7, wherein $R_z$ is a branched or linear alkyl group having 1 to 20 carbon atoms.

9. The composition of claim 7, wherein the degree of ethoxylation varies between the two ethoxylated tails of the surfactant composition.

10. The composition of claim 7, wherein the quaternary ammonium containing compound is an alkylated quaternary ammonium compound, ring or cyclic quaternary ammonium compound, aromatic quaternary ammonium compound, diquaternary ammonium compound, alkoxylated quaternary ammonium compound, amidoamine quaternary ammonium compound, ester quaternary ammonium compound, alkanolamine, triamine and/or mixtures thereof.

11. A method of employing a sanitizing composition comprising:
contacting a surface, article and/or substrate with the sanitizing composition of claim 1.

12. The method of claim 11, wherein the surface is contacted by a use solution of the sanitizing composition diluted with water to 0.1 g/L to 100 g/L.

13. The method of claim 11, wherein the sanitizing composition is a composition selected from the group consisting of: a hard surface cleaning composition, a laundry detergent cleaning composition, a ware wash detergent composition, a rinse additive composition, a hand care detergent composition, an air freshening composition, a disinfecting composition, a vehicle cleaning composition, a degreasing composition, a floor cleaning composition, and a CIP detergent composition.

14. The method of claim 11, wherein the article and/or surface is a floor, countertop, sink, other architectural hard surface, ceramic, glass, metal, wood, hard plastic, fabric or textile.

15. The method of claim 11, wherein the sanitizing composition is a liquid.

16. The method of claim 11, wherein the sanitizing composition is an antimicrobial, sterilant, sanitizer, disinfectant, preservative, deodorizer, antiseptic, fungicide, germicide, sporicide, virucide, detergent, bleach, hard surface cleaner, hand soap, waterless hand sanitizer, pre- or post-surgical scrub, veterinary product, food and/or processing treatment product, plant and/or processing treatment product, water treatment, industrial process treatment, textile detergent, paint, glue, lubricant, coolant, fiber glass sizing composition, drilling fluid, gas hydrate inhibitor, corrosion inhibitor, or personal care composition.

* * * * *